United States Patent
Landers et al.

(10) Patent No.: US 7,223,325 B2
(45) Date of Patent: May 29, 2007

(54) METHOD FOR ORTHOGONAL ANALYTE STACKING/INJECTION SYSTEMS IN ELECTROPHORESIS

(75) Inventors: James P. Landers, Charlottesville, VA (US); James F. Palmer, Laguna Beach, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 559 days.

(21) Appl. No.: 10/432,141

(22) PCT Filed: Nov. 19, 2001

(86) PCT No.: PCT/US01/43259

§ 371 (c)(1),
(2), (4) Date: May 16, 2003

(87) PCT Pub. No.: WO02/48673

PCT Pub. Date: Jun. 20, 2002

(65) Prior Publication Data

US 2004/0035703 A1    Feb. 26, 2004

Related U.S. Application Data

(63) Continuation-in-part of application No. 09/418,659, filed on Oct. 15, 1999, now Pat. No. 6,569,305.

(60) Provisional application No. 60/249,611, filed on Nov. 17, 2000.

(51) Int. Cl.
*G01N 27/453*    (2006.01)
*G01N 27/447*    (2006.01)
(52) U.S. Cl. ............... 204/453; 204/451; 204/604; 204/601; 204/549; 204/645
(58) Field of Classification Search ........ 204/451–455, 204/601–605, 549, 645
See application file for complete search history.

(56) References Cited

U.S. PATENT DOCUMENTS 6,569,305 B1 *   5/2003   Palmer et al. .............. 204/454

OTHER PUBLICATIONS

Shihabi ("Sample stacking by acetonitrile-salt mixtures," J. Cap. Elec. 002:6 1995, pp. 267-271).*
Abstract of Smith et al. ("Instrumentation for High-Performance Capillary Electrophoresis Mass-Spectrometry," J. Chrom., 1991, 559, 197-208.*
Palmer et al. ("A Universal Concept for Stacking Neutral Analytes in Micellar Capillary Electrophoresis," Analytical Chemistry, vol. 71, No. 9), 1999.*

* cited by examiner

*Primary Examiner*—Alex Noguerola
(74) *Attorney, Agent, or Firm*—Robert J. Decker

(57) ABSTRACT

In the present capillary electrokinetic chromatograpy method, analytes are injected by electroosmotic flow directly from a sample matrix into a separation buffer containing an electrokinetic vector with an opposite mobility. Analytes can now be injected at the velocity of electroosmotic flow, but are retained at the interface of the sample matrix-co-ion and separation buffer micelle zones as analyte/micelle complexes. Manipulation of the injecting force and opposing stacking force allow greatly increased length or volume of injection. Concentrations of the micelle, methanol, and borate in the separation buffer were provided to increase maximum injection length of neutral analytes. Reducing the analyte velocity in the separation buffer without substantially decreasing the velocity of the analyte during injection from the sample vial allowed greatly extended sample plug injection lengths. It is further enabled to inject sample solvent volumes equivalent to about twenty times the effective capillary volume. Equations and algorithms describing the injection process and maximum injection lengths for this mode of stacking in electrokinetic capillary chromatography are introduced. Use of the present method provides for maximum electrokinetic stacking injection for a wide variety of analytes and separation systems.

91 Claims, 14 Drawing Sheets

METHOD FOR ORTHOGONAL ANALYTE STACKING/INJECTION SYSTEMS IN ELECTROPHORESIS

RELATED APPLICATIONS

This application is a national stage filing of International Application No. PCT/US01/43259, filed Nov. 19, 2001, which claims benefit under 35 U.S.C. Section 119(e) from U.S. Provisional Application Ser. No. 60/249,611, filed on Nov. 17, 2000, entitled "Orthogonal Analyte Stacking/Injection Systems in Capillary Electrophoresis," the entire disclosures of which are hereby incorporated by reference herein in their entirety. The present application is a continuation-in-part of U.S. patent application Ser. No. 09/418,659, filed Oct. 15, 1999, entitled "Method and Injection and Stacking of Analytes in High-conductivity Samples," the entire disclosure of which is hereby incorporated by reference herein, and which is now U.S. Pat. No. 6,569,305B1.

FIELD OF INVENTION

This invention relates to an improved method and system for stacking analytes in electrophoresis, and more particularly an orthogonal analyte stacking/injection system that allows the loading of volumes that exceed that of the separation capillary, channel, well or whatever conduit is used for separation of the analytes (i.e., multiple column volumes).

BACKGROUND OF INVENTION

In broad terms, analytical chemistry involves some combination of separation, identification, and quantitation of analytes of particular interest. To accomplish these goals, it is necessary to provide a sufficient concentration of the analytes at the detection point in the analytical device to register a signal at the detector that is distinguishable from background signal. With analyte concentrations below parts per million (ppm), many analytical detection systems are inadequate to detect the analyte.

Capillary electrophoresis (CE) is a high-resolution technique for separating charged analytes in liquid solutions using electric fields. The micron-scale radial dimensions of the capillary serve to dissipate Joule heating and control convection efficiently at high separation voltages, allowing for plate heights of micrometers or less. However, because of the small radial dimension of a capillary, it is difficult to detect short injected plug lengths of low-concentration analytes using standard optical detection set-ups (e.g., UV-VIS absorbance detection). Hence, the injection of large sample volumes (i.e., long sample plugs) has been necessary to improve the detection of analytes present at low concentration. Normally, the injected length of an analyte plug injected into some form of separation column, determines the minimum peak width at the detection point. As a result of the fact that separation columns are of a finite length, injection plug length is limited, in practical terms, to the millimeter range—beyond this, the high-resolution capabilities of capillary electrophoresis cannot be preserved. However, this problem has been circumvented by protocols that invoke mechanisms that narrow, or stack, much longer analyte zones into sample plugs. Stacking concentrates the analytes into smaller space, decreasing the length of an analyte zone and, thus, increasing the analyte concentration and its signal at the detector.

FIG. 8 shows an exemplary setup that can be used to practice electrophoresis. Electrophoresis unit 1 is interfaced with data collection/storage unit 14, which contains software/firmware/hardware for control of the instruments and data collection (e.g., processor, personal computer, display monitor and printer, or personal digital assistant (PDA) or the like. Separation channel 2 (shown here as a capillary) has an entrance (inlet) end 4, an exit (outlet) end 6, and a detection window 8. Separation channel 2 is flushed by high pressure or vacuum with three to five capillary volumes of buffer. The outlet reservoir 10 is filled with buffer and holds the exit end 6 of separation channel 2. Inlet reservoir 12 is also filled with buffer and holds the entrance end 4 of separation channel 2. Sample reservoir 11 contains sample for injecting into the separation channel 2. The high voltage power unit 16 has an anode 18 and a cathode 20. Outlet reservoir 10 also holds cathode 20, while inlet reservoir 12 also holds anode 18. An electric field is then applied by high voltage power unit 16 across separation channel 2 from anode 18 to cathode 20, which causes buffer in inlet reservoir 12 to travel through separation channel 2 and into outlet reservoir 10, for electrophoretic conditioning of separation channel 2. After separation, channel 2 has been electrophoretically conditioned, anode 18 and entrance end 4 of separation channel 2 are placed within sample reservoir 11. An electric field may be applied across separation channel 2 for electrokinetic injection (injection by electrophoresis instead of by pressure) of a sample plug into separation channel 2. The electric field is applied across separation channel 2 for a period of time sufficient to permit injection of a sample plug of desired length. Alternatively, the plug could be injected into separation channel 2 using a pressure technique known in the art.

Once an analytes zone is located at the detection window 8, radiation, for example from an ultraviolet (UV) light source 34, shines through on the detection window 8 and, therefore, through the analytes—the amount of light transmitted through the sample and window is detected by the detector 36 located on the opposite side of detector window 8 from UV source 34. The detector 36 is interfaced with a data collection/storage unit 14 to collect the separation data including the number of analytes zones to traverse the window as well as the relative amount of light that was incident on the detector (which translates to "concentration").

FIG. 9 is an illustrative setup used to practice electrophoresis. The electrophoretic unit 101 is a T-configuration cross-channel injection microchip. Separation Channel 102 has an entrance end 104, an exit end 106. Outlet reservoir 110 is filled with buffer and is connected to exit end 106 of separation channel 102. Inlet reservoir 112 is also filled with buffer and is connected to entrance end 104 of separation channel 112. Sample channel 140 has an entrance end 142 and an exit end 144. Sample reservoir 111 contains sample for injecting into separation channel 102 and is connected to entrance end 142 of sample channel 140. Waste reservoir 146 is filled with buffer and is connected to exit end 144 of sample channel 140. Sample channel 140 is configured to connect through and cross over separation channel 102 to form a 'T-configuration'. High voltage power unit 116 has an anode connected to inlet reservoir 104 and an anode connected to sample reservoir 111, and a cathode connected to outlet reservoir 110 and a cathode connected to waste reservoir 146. An electric field is applied across separation channel 102 for electrophoretic conditioning. The field is applied from anode connected to inlet reservoir 112 to cathode connected to outlet reservoir 106. For electrokinetic injection of a sample plug into separation channel 102 (not by pressure which is the current state-of-the-art), an electric field is applied from anode connected to sample reservoir 111 to cathode connected to outlet reservoir 106 for a defined period of time. An electric field is then applied across separation channel 102 causing separation and detection of the various analyte zones. The field is applied from anode connected to inlet reservoir 112 to cathode connected to outlet reservoir 106.

To separate neutral analytes by CE, it is necessary to provide an electrokinetic vector. The first example of this, micellar electrokinetic chromatography, utilized a charged micelle to impart mobility to neutral analytes. As a result of the successful use of other electrokinetic vectors that are not micellar in character, (e.g., charged cyclodextrins) electrokinetic chromatography (EKC) is a term that has been utilized to encompass the use of any electrokinetic vector for separation of neutral analytes. Recent techniques for stacking neutral analytes in EKC require pressure injections of sample matrixes. For instance, high-salt stacking and sweeping have been applied to afford sample plug lengths up to 60% of the effective capillary length (length from the injection end to the detection point). High-salt stacking utilizes discontinuous buffer conditions (the separation matrix co-ion is different from the sample matrix co-ion). The sample matrix co-ion (the ion with the same charge as the electrokinetic vector, e.g., chloride) must have a higher intrinsic electrophoretic mobility than the electrokinetic vector, and the sample co-ion must be present at a higher concentration in the sample matrix than that of the electrokinetic vector in the separation buffer.

Also, sweeping utilizes continuous sample matrix/separation buffer conditions, i.e., there are no mobility differences between the background electrolyte or buffer, between the sample matrix and the separation buffer.

In addition, pressure injections are typically low-velocity to diminish mixing at the sample matrix/separation buffer interface and to maintain reproducibility between analyses. While typical separations take as little as 60 seconds, the time necessary to introduce long sample plugs (e.g., 50% of the capillary length, ca. 50–2000 seconds) by low pressure can, in certain instances, exceed the analysis time by more than an order of magnitude.

Another drawback associated with large sample plug pressure injections is that the effective capillary length available for separation is reduced, having undesirable effects on the ability to resolve analytes. While longer capillaries might be used to overcome this problem, the 30 kV limit associated with most CE instrumentation does not allow for the same high fields (800–1000 volts/cm) typically needed for rapid, high-resolution analyses to be applied.

In addition, longer capillary lengths are not conducive with translating stacking methods from the traditional capillary format to the microchip format.

There is, therefore, a need in the art to inject large volume sample plugs (exceeding the length of the separation column) while still retaining a maximal effective capillary length for the separation mode. The electroosmotic flow can be used to inject neutral analytes in EKC without stacking, however, a concomitant stacking of neutral analytes during electrokinetic injection by electroosmotic flow is possible—this is described herein. Furthermore, the electrokinetic injection of high-salt sample matrixes by electroosmotic flow is provided, with the stacking of neutral analytes occurring simultaneously with the injection procedure, in both high-salt stacking and sweeping modes.

SUMMARY OF THE INVENTION

A novel approach for analyte stacking method for electrokinetic chromatography with the capillary format has now been discovered. In one preferred embodiment, the present invention method of stacking analytes in electrophoresis, comprises: filling a conduit with a separation buffer, the buffer comprising buffer components; orienting a first end of said conduit in operative relation with (e.g., articulated with or in synthesis with) the separation buffer; orienting a second end of the conduit in operative relation with (e.g., articulated with or in synthesis with) an analyte sample; applying an electric field across the separation buffer and the analyte sample through the conduit. Furthermore, portions of the analyte sample inject into the second end of said conduit, whereby the velocity of the analyte defines an injection vector, and the buffer components have a net movement opposite that of the injection vector, whereby analytes being injected encounter the buffer component and experience a decrease in velocity, the decrease in velocity constitutes a vector known as a stacking vector. The present invention method farther comprises, adjusting the mobility of either said injection vector or the stacking vector (or both) to allow maximum amount of the injected analyte.

In another aspect, the present invention provides an apparatus for stacking analytes in electrophoresis, comprising: means for filling a conduit with a separation buffer, the buffer comprising buffer components; means for orienting a first end of the conduit in operative relation with (e.g., articulated with or in synthesis with) the separation buffer; means for orienting a second end of said conduit in operative relation with (e.g., articulated with or in synthesis with) an analyte sample; means for applying an electric field across the separation buffer and the analyte sample. Furthermore, portions of the analyte sample inject into the second end of the conduit, whereby the velocity of said analyte defines an injection vector, and the buffer components have a net movement opposite that of the injection vector, whereby analytes being injected encounter the buffer component and experience a decrease in velocity, the decrease in velocity constitutes a vector known as a stacking vector. The present invention further comprises means for adjusting the mobility of either the injection vector or the stacking vector (or both) to allow maximum length of said injected analyte.

The present invention electrokinetic injection method is faster than previous injection methods by approximately an order of magnitude.

Another advantage of the present invention method is that it allows the loading of multiple-capillary volumes of sample for the first time.

Moreover, another advantage of the present invention method is that it provides a higher resolution for injection of large sample plugs in capillary electrophoresis, providing a faster and higher sensitivity injection mode in capillary electrokinetic chromatography.

Previously, long sample plugs could be injected into a capillary by pressure, with post-injection stacking of analytes occurring due to electrophoretic phenomena. However, the present invention provides a method and system where stacking can be initiated with injection, rather than post-injection. The present invention further provides electrokinetic injection of neutral analytes with concomitant stacking of neutral analytes can be initiated at the commencement of injection. See Palmer, J.; Burgi, D. S.; Munro, N. J.;

Landers, J. P., "*Electrokinetic Injection for Stacking Neutral Analytes in Capillary and Microchip Electrophoresis*", Anal. Chem. 2001, 73,725–731.

Further still, the present invention method provides an electrokinetic injection of neutral analytes by electroosmotic flow in the presence of an orthogonal stacking system, i.e., an anionic electrokinetic vector in the separation buffer, constitutes an orthogonal analyte stacking/injection system (OAS/IS). The requisite conditions are simply that the electrokinetic vector in the separation buffer has a mobility opposite that of the analyte injection force, and that a suitable stacking boundary is formed between the injected sample and the electrokinetic vector in the separation buffer. As will be discussed later, an extensive list of conditions for OAS/IS is included in Tables 1–6. With properly instituted OAS/IS conditions, it is actually possible to inject sample volumes (plugs) that exceed that of the entire capillary. A schematic of this concept is shown in FIG. 1.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

As shown in FIG. 1, the horizontal bar A depicts an analyte zone (AZ) length for a 100% capillary effective length injection without stacking. As shown in FIG. 1, the horizontal bar B depicts a 100% capillary effective length injection with stacking occurring at a co-ion boundary with a velocity half that of the electroosmotic flow. As shown in FIG. 1, the horizontal bar C, depicts a position of co-ion boundary and stacked analytes after transition of the sample plug through the co-ion boundary.

FIG. 14A demonstrates the location of the stacked analyte at the conclusion of a 171 cm injection. The stacked analyte/micelle peak has progressed 20.38 cm into the capillary. Likewise, 20.38 cm of unstacked sample plug remain to pass into the micelle zone to be stacked. FIG. 14B illustrates the movement of the stacking analyte peak and the sample plug. FIG. 14C shows the position of the analyte/micelle peak at the conclusion of the passage of the sample matrix. The analyte/micelle peak has moved 23.14 cm into the capillary, leaving ~1.4 cm remaining for separation. For injections longer than the predicted maximum of 180 cm, the injection-side of the sample plug does not have time to pass through the stacked analyte/micelle peak before the peak has entered the detector. A 196 cm injection is depicted in FIG. 14D. At the conclusion of this injection, the analyte/micelle peak has moved 23.4 cm into the capillary. The moment the peak has entered the detector window, the length of sample plug that has still not passed through the analyte/micelle peak is 16.7 cm as shown in FIG. 14E. Thus, the effective length of sample plug that appears in the stacked peak at the detector is equivalent to 197 cm−16.7 cm=180.3 cm, the predicted maximum injection length under these conditions. The detector response to unstacked analytes at sample matrix concentration is negligible, as shown in FIG. 14F, making all longer injections appear identical.

DETAILED DESCRIPTION OF THE INVENTION

The present invention provides a method and system of injecting analytes into a capillary or conduit filled with separation buffer for stacking and separation by electrokinetic chromatography. The method of injection utilizes electroosmotic flow to inject analytes against a stacking front composed of an anionic electrokinetic vector. This method is instituted electrokinetically by injecting the analytes directly from a sample matrix into the capillary or other microchannel electrophoresis apparatus by applying an electric field. The present invention provides the first instance of an orthogonal analyte stacking/injection system (OAS/IS) and related method thereof. This system and method and other potential OAS/IS conditions are described herein.

Figure 1:
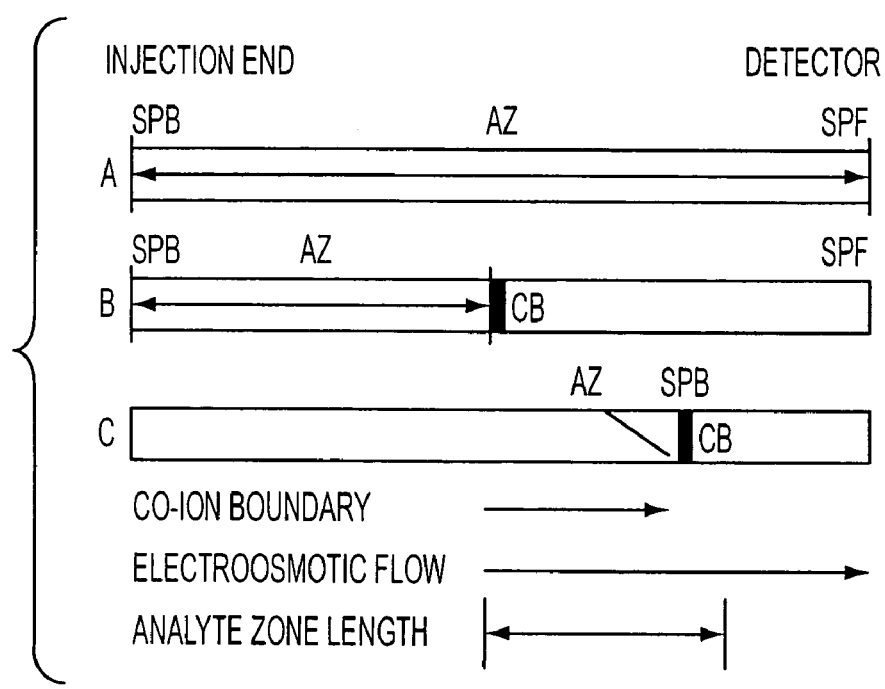
FIG. 1 is a theoretical depiction of co-ion boundary movement into a capillary. The lower velocity of the co-ion boundary (CB) allows sample plugs longer than 100% of the effective capillary length. Anode is at the injection end. The boundaries include a sample plug font (SPF) and sample plug back (SPB). Arbitrarily, the co-ion boundary velocity is half that of the electroosmotic flow velocity. This is a plausible situation when the co-ion boundary has an anodic mobility.

As shown in FIG. 1, orthogonal analyte stacking and injecting can allow for the injection of sample plugs that are equal to or greater than the entire length of the capillary. Or said differently, this technique allows for large sample volumes (large by microanalytical technique standards) to be injected for analysis. Heretofore, the conventional rule or standard with most separations is that no more than 1–5% of the total column volume can be injected as a sample plug. However, with the present invention stacking method described herein, OAS/IS, sample plug volumes equivalent to and exceeding 100% of the column volume (i.e., multiple column volumes) can be injected and effectively analyzed without compromising resolution. This stands to impact electrophoretic separations carried out in capillaries, but even more so, those carried out on microchips.

In general, stacking of analytes during the injection procedure would maximize the effective capillary length available for separation. To accurately quantify the amount of an analyte that is electrokinetically injected, two sources of bias for electrokinetic injection have been identified, analyte charge, and the effect of the sample matrix on electroosmotic flow. Equation (1) describes analyte loading by pressure injections:

$$Q_i = l_i * A * C_I \qquad 1)$$

where $Q_i$ is the moles of analyte, i that are injected, $l_i$ is the length of the capillary that analyte i occupies at the conclusion of injection, A is the cross sectional area of the capillary, and $C_i$ is the molarity of analyte i in the injection vial.

Equation (2) describes electrokinetic injections in continuous systems (i.e., in the absence of an isotachophoresis (ITP) effect):

$$Q_i = [(\mu_i + \mu_{eof})*E*t_{inj}]*A*C_i \qquad (2)$$

where the term $[(\mu_i + \mu_{eof})*E*t_{inj}]$ replaces $1_i$ in equation (1), again under the con of continuous systems, with $\mu_i$ the electrophoretic mobility of analyte i, $\mu_{eof}$ the electrophoretic mobility of the electroosmotic flow, E the applied electric field, and $t_{inj}$ the amount of time the electric field for injection is applied. For neutral analytes, the term $\mu_i$ in equation (2) disappears, and it is indicated that the length of the sample plug is directly proportional to electroosmotic flow velocity. Consequently, we are provided with:

$$Q_i = \mu_{eof}*E*t_{inj}A*C_i. \qquad (3)$$

However, if the sample matrix co-ion is discontinuous from the separation buffer, there is a potential bias from the effect of the sample matrix on electroosmotic flow. It has been shown that bulk electroosmotic flow velocity is an average of the electroosmotic flow velocities of the sample matrix and the separation buffer, proportional to the length of the capillary each occupy. Hence;

$$Q_i = v_B*C_i*A*t_{inj} = [(x*v_s)+((1-x)*(v_{sep}))]*C_i*A*t_{inj} \qquad (4)$$

where $v_B$ is the bulk electroosmotic flow velocity, x is the length of the sample plug injected that is expressed as a fraction of the total capillary length, $v_s$ is the velocity of the electroosmotic flow solely in the presence of sample matrix, and $v_{sep}$ is the velocity of the electroosmotic flow solely in the presence of separation buffer. Including the electric field effect on velocity leads to:

$$Q_i = [(x*\mu_{eof,S}) + ((1-x)*\mu_{eof,sep})]*E*C_i*A*t_{inj} \qquad (5)$$

However, because the high-salt sample matrix has a resistance that differs from the separation buffer, the different electric fields in the two zones require equation (5) to be rewritten as:

$$Q_i = [(x*\mu_{eof,S})*E_S] + [((1-x)*\mu_{eof,sep})*E_{sep}]*C_i*A*t_{inj} \qquad (6)$$

In the instant disclosure, the electrokinetic stacking injection of neutral analytes in electrokinetic chromatography (EKC) is described. Electroosmotic flow is used to inject long sample plugs under continuous and discontinuous conditions. The simultaneous stacking of neutral analytes at a co-ion interface with the electrokinetic vector in the separation buffer during injection is described. The decreased analysis times using electrokinetic injection, as well as the enhanced detection limits and reproducibility versus pressure injection are shown. The results are derived from the use of neutral analytes, with an anionic electrokinetic vector, in the presence of electroosmotic flow, under normal polarity (with the anode at the inlet). In addition, a comprehensive outline of potential OAS/IS method and system conditions are provided for alternative embodiments. The instant disclosure describes the potential of OAS/IS methods and systems for anionic and cationic analytes, and cationic and neutral electrokinetic vectors. Also provided is the potential of orthogonal analyte stacking and injecting methods and systems in the absence of EOF, and the potential of orthogonal analyte stacking and injecting under reversed polarity.

While the length of the sample plug injection increases proportionally with the duration of the injection multiplied by the EOF rate (inj time×EOF), the analytes are stacked at the pseudo steady-state boundary that is moving against the EOF. This feature allows stacking to be initiated at the capillary inlet at the beginning of the injection. As injection continues, the boundary moves into the capillary because the electrophoretic mobility of the boundary is less than the electrophoretic mobility of the EOF. The effective capillary length remaining for separation at the conclusion of injection can be determined by:

$$(\mu_{EOF}*E)*t_i = L_i \qquad (7)$$

$$t_i*1/(\mu_{psb}*E) = t_{trans} \qquad (8)$$

$$t_{trans}*(\mu_{EOF}+\mu_{psb})*E = L_{trans} \qquad (9)$$

where $\mu_{EOF}$ is the electrophoretic mobility of EOF, E is the applied field, $t_i$ is the number of seconds of injection, $L_i$ is the length of the injection, $\mu_{psb}$ is the electrophoretic mobility of the pseudo steady-state boundary, $t_{trans}$ is the amount of time it takes the pseudostationary boundary to completely transit the sample plug, and $L_{trans}$ is distance into the capillary the stacking boundary has moved upon completely transiting the sample plug.

Figure 2:
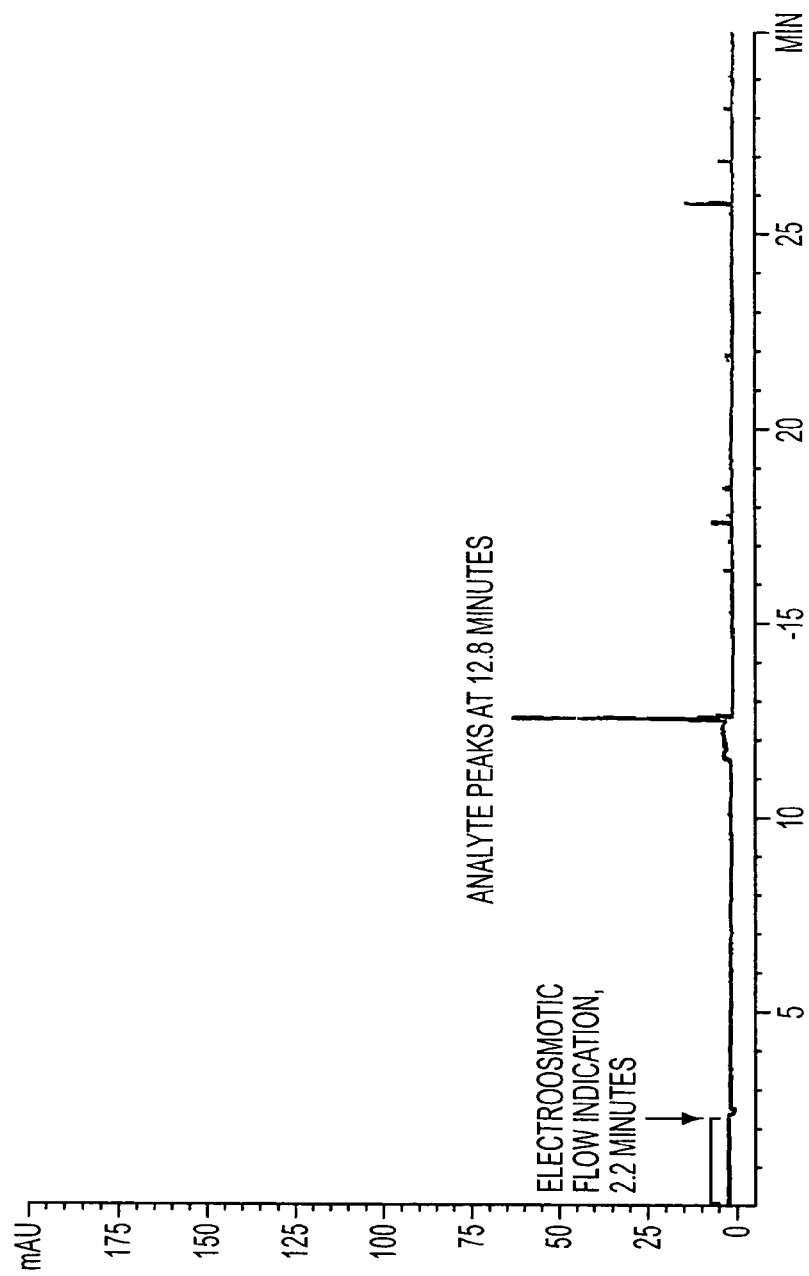
FIG. 2 is an electropherogram where the absorbance at the detector [in milli-absorbance units (mAU)] is plotted versus time after a multiple capillary-length sample plug injection has been initiated followed by separation—resolution of corticosteroid analytes is seen. With conditions optimized for minimum velocity analyte elution in combination with strong electroosmotic flow, it is possible to inject multiple capillary-length sample plugs. In this figure, electroosmotic flow is shown at the detector at 2.2 minutes, while analyte peaks arrive at 12.8 minutes, indicating a 5.8 capillary-length injection (191 cm sample plug in a 33 cm capillary). The general conditions are as follows: separation buffer containing 40 mM sodium dodecyl sulfate (SDS), and 240 mM borate; the sample matrix consisting of 270 mM borate and containing four corticosteroids at 50 ppb; and a 33 cm capillary having a 50 μm i.d. Also provided is a continuous injection from the sample matrix into the separation buffer under normal polarity at 15 kV.

FIG. 2 is an electropherogram where the absorbance at the detector [in milli-units(mAU)] is plotted versus time for a continuous injection from the sample matrix into the separation buffer. The electroosmotic flow indicator is shown at 2.2 minutes, while the analyte peaks do not appear until 12.8 minutes. This indicates a sample plug length of approximately 191 cm in a capillary that is only 33 cm long. In addition, the peak height of the analytes is large (~70 MAU) for an analyte concentration of only 50 ppb, indicating a limit of detection in the parts per trillion (ppt) range. This sensitivity has never before been reported for neutral analytes in capillary electrophoresis.

Figure 3:
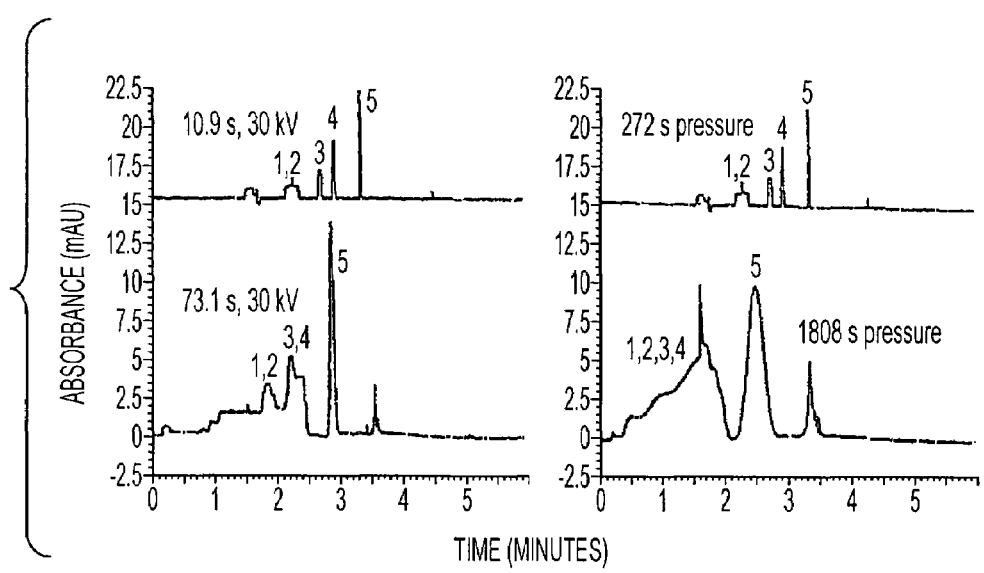
FIG. 3 is an electropherogram showing absorbance (mAU) versus time when comparing the differences in effectiveness of electrokinetic versus pressure injections. The general conditions are as follows: 150 mM sodium chloride sample matrix, duration of 30 kV or 50 mbar injections as listed in the figure. The separation conditions are: 80 mM sodium cholate, 10% ethanol, 5 mM tetraborate, pH ~9 separation buffer, in a 19 mm (i.d.) by 33 cm capillary; separation at 30 kV. The total analysis times with an 80% effective-length plug injection by pressure was 1928 seconds. With electrokinetic injection, the total analysis time was 250 seconds; peak order for 1–5, cortisone, cortisol, 11-deoxycortisol, 17-hydroxyprogesterone, and progesterone. This graph indicates that electrokinetic injection not only allows for higher-resolution to be obtained when compared to pressure injection, but it is also approximately an order of magnitude faster.

FIG. 3 is an electropherogram showing absorbance (mAU) versus time that illustrates the differences in effectiveness of using electrokinetic injection compared to pressure injection, whereby electrokinetic injection can be up to an order of magnitude faster than conventional art. In addition to the traditional capillary electrophoresis format, much interest has been generated in translating separation and stacking mechanism to the microchip format.

For EKC in the presence of electroosmotic flow (EOF) under normal polarity, i.e., the inlet is anodic, a negatively-charged electrokinetic vector such as a micelle is commonly used. A neutral analyte acquires an effective mobility when it interacts with the electrokinetic vector, in this case a micelle. When an electric field is applied, the micelle is mobilized against the EOF. Stacking techniques in this mode using pressure injection of the sample matrix have been developed based on the difference in mobility of neutral analytes in a sample matrix, devoid of a micelle, with either equivalent conductivity (See Quirino, J. P.; Terabe, S. *Science* 1998, 282, 465–468) or higher conductivity (See Palmer, J., Munro, N. J., Landers, J. P. *"A universal Concept for Stacking Neutral Analytes in Micellar Capillary Electrophoresis"*, Anal. Chem. 1999, 71, 1679–87 and U.S. application Ser. No. 09/418,659 by Palmer et al.) relative to the separation buffer. Analytes are stacked as they encounter the electrokinetic vector in the separation buffer and become charged analyte/electrokinetic vector complexes. The "sweeping" technique described by Quirino and Terabe is based on a strong interaction between the analyte and micelle (high partition coefficient). The high-salt stacking technique (Palmer, J., Munro, N. J., Landers, J. P. *"A universal Concept for Stacking Neutral Analytes in Micellar Capillary Electrophoresis"*, Anal. Chem 1999, 71, 1679–87 and U.S. application Ser. No. 09/418,659 by Palmer et al.)

depends upon the initial formation of a pseudo steady-state boundary between the sample matrix co-ion and the separation buffer micelle.

While electrophoretic mobility is commonly used to normalize electrophoretic processes per an applied field, it is also possible to describe these processes in terms of the velocity of components during electrophoresis. In the instant disclosure, the velocity of components is used to simplify concepts introduced below. Velocity (cm/sec) is measured from the inlet (anodic), to the detector at the cathodic side of the capillary. All components have a positive velocity due to EOF. Positive velocity of neutral analytes can be reduced by interaction with an anionic micelle. For example, the maximum velocity of a neutral analyte is the velocity of the EOF. The minimum velocity for a neutral analyte is the velocity of the micelle (neglecting the size and mass of the analyte) if an analyte is completely complexed with the micelle. The velocity of the micelle is simply a sum of the anodic mobility of the micelle and the mobility of the bulk fluid toward the cathode (EOF) multiplied by the electric field.

Pressure injections of long sample plugs have previously been used in capillary electrokinetic chromatography to set the stage for analyte stacking during electrophoresis. However, during pressure injections, the interface between the sample matrix and the separation buffer (where analyte stacking is initiated) progresses into the capillary at a velocity equivalent to the flow rate of injection. During pressure injections, the electrokinetic vector simply has the mobility of the bulk flow. With extended injections, the capillary length remaining for stacking and separation at the termination of injection can be severely reduced, resulting in compromised resolution of analytes. To counter this problem, electrokinetic injection of neutral analytes via EOF was previously investigated. See Palmer, J., Landers, J. P, "*Stacking Neutral Analytes in Capillary Electrokinetic Chromatography with High Salt Sample Matrixes*", Anal. Chem. 2000, 72, 1941–1943 and Palmer, J.; Burgi, D. S.; Munro, N. J.; Landers, J. P., "*Electrokinetic Injection for Stacking Neutral Analytes in Capillary and Microchip Electrophoresis*", Anal. Chem. 2001, 73,725–731. It is possible to perform electrokinetic stacking injections with both discontinuous and continuous conditions in EKC. To implement continuous conditions for stacking, neutral analytes are prepared in a sample matrix containing the same background electrolyte or buffer (e.g., borate) as the separation buffer.

In one preferred embodiment of the present invention, sodium dodecyl sulfate (SDS) was used as the micelle, with borate as the background electrolyte. The borate concentration in the sample matrix was adjusted to provide equivalent conductivity to the separation buffer that contained both borate and the charged micelle. This condition is referred to as "continuous conductivity" to distinguish it from the use of a discontinuous sample matrix co-ion (i.e., high-mobility) such as chloride.

The neutral analytes chosen as model compounds for the study disclosed herein are members of the vertebrate corticosteroid metabolic pathway, step-wise hydroxylated from progesterone to 17α-hydroxyprogesterone, 11-deoxycortisol, and finally to cortisol. The step-wise hydroxylation of each analyte decreases the hydrophobic interaction with the micellar phase. The background electrolyte, borate does not act as an electrokinetic vector for the selected analytes. The migration order of the analytes under normal polarity electrophoresis with SDS as the electrokinetic vector indicates that elevated hydrophobic interactions between the analytes and SDS cause an increase in analyte migration time, i.e., the more hydrophobic analytes display longer migration times.

The use of SDS in the separation buffer in conjunction with EOF injection of neutral analytes under normal polarity with continuous conductivity conditions was examined. The greater the ratio of the velocity of the injection vector, EOF, to the velocity of the analyte/electrokinetic vector complex, the longer an injection can be carried out. Consequently, the maximum length injection is postulated as:

$$L_{max}=(v_{EOF}/v_{a/ekv}-1)*L_{det} \quad (10)$$

where $L_{max}$ is the maximum injectable plug length, $v_{EOF}$ is the velocity of EOF, $v_{a/ekv}$ is the velocity of the analyte due to interaction with the electrokinetic vector (charged micelle) and $L_{det}$ is the length of the capillary to the detector. With a maximum length injection, the injection-end of the sample plug arrives at the detector simultaneously with a given analyte/micelle complex.

One approach to increase injection length would be to augment EOF by utilizing pressure or a capillary surface coating. However, all components are affected by bulk flow, including the analyte/electrokinetic vector complex. Increasing the EOF would simply move all components toward the detector and reduce capillary length remaining for separation of analytes. Reducing EOF is undesirable because it would lengthen the amount of time required to inject a sample plug. It is apparent that the $v_{a/ekv}$ should be reduced without an equivalent decrease in $v_{EOF}$ to afford an increased sample plug length as well as to maintain injection speed.

The present invention method and system minimizes analyte/micelle complex velocity without substantially reducing the EOF velocity. Separation buffer parameters including the concentration of the micellar species, organic modifier, and background electrolyte were examined herein. In all experiments, the sample matrix conductivity was adjusted to the equivalent separation buffer conductivity by addition of the same background electrolyte used in the separation buffer (borate). With optimized separation buffer conditions, multiple capillary-length electrokinetic stacking injections were investigated.

The present invention provides for the electrokinetic injection of neutral analytes by electroosmotic flow under normal polarity in electrokinetic chromatography with a negatively-charged electrokinetic vector. Under these conditions, the electrokinetic vector is moving opposite, or orthogonally to the electroosmotic flow. This is the first demonstration of orthogonal analyte stacking/injection systems (OAS/IS). However, it should be appreciated that there are potentially many other types of analyte injection schemes that constitute OAS/IS method and systems. Conditions for OAS/IS methods and systems by electrokinetic and pressure injections are outlined below in Tables 1–6, with directions given for different polarity, electrokinetic vector charge, and analyte charge, as well as positive and negative pressure.

TABLE 1

I. Electroosmotic Flow Injection

A. Injection under normal polarity

1. Anionic electrokinetic vector with neutral analytes
2. Anionic electrokinetic vector with cationic analytes
3. Neutral electrokinetic vector with cationic analytes B. Injection under reversed polarity 1. Cationic electrokinetic vector with neutral analytes
2. Cationic electrokinetic vector with negative analytes
3. Neutral electrokinetic vector with negative analytes

TABLE 2

II. Pressure Injection In The Presence Of Electroosmotic Flow

A. Positive pressure injection, normal polarity applied

1. Anionic electrokinetic vector with neutral analytes
2. Anionic electrokinetic vector with cationic analytes
3. Neutral electrokinetic vector with cationic analytes B. Positive pressure injection, reversed polarity applied 1. Cationic electrokinetic vector with neutral analytes
2. Cationic electrokinetic vector with negative analytes
3. Neutral electrokinetic vector with negative analytes C. Negative pressure injection, normal polarity applied 1. Cationic electrokinetic vector with neutral analytes
2. Cationic electrokinetic vector with negative analytes
3. Neutral electrokinetic vector with negative analytes D. Negative pressure injection, reversed polarity applied 1. Anionic electrokinetic vector with neutral analytes
2. Anionic electrokinetic vector with cationic analytes
3. Neutral electrokinetic vector with cationic analytes

TABLE 3

III. Pressure Injection In The Absence Of Electroosmotic Flow

A. Positive pressure injection, normal polarity applied

1. Anionic electrokinetic vector with neutral analytes
2. Anionic electrokinetic vector with positive analytes
3. Neutral electrokinetic vector with positive analytes B. Positive pressure injection, reversed polarity applied 1. Cationic electrokinetic vector with neutral analytes
2. Cationic electrokinetic vector with negative analytes
3. Neutral electrokinetic vector with negative analytes C. Negative pressure injection, normal polarity applied 1. Cationic electrokinetic vector with neutral analytes
2. Cationic electrokinetic vector with negative analytes
3. Neutral electrokinetic vector with negative analytes D. Negative pressure injection, reversed polarity applied 1. Anionic electrokinetic vector with neutral analytes
2. Anionic electrokinetic vector with cationic analytes
3. Neutral electrokinetic vector with cationic analytes

TABLE 4

IV. Modification Of Electroosmotic Flow To Induce Orthogonal Analyte Stacking/Injection A. Utilizing pressure to counteract electroosmotic flow to induce orthogonal analyte stacking/injection

TABLE 4-continued

IV. Modification Of Electroosmotic Flow To Induce Orthogonal Analyte Stacking/Injection B. Chemically modifying EOF 1. Dynamic coating of a capillary to reduce EOF
2. Dynamic coating of a capillary to reverse EOF
3. Dynamic coating of a capillary to increase EOF C. Covalently modifying EOF 1. Coating of a capillary to reduce EOF
2. Coating of a capillary to reverse EOF
3. Coating of a capillary to increase EOF D. Control of EOF in a sample microchannel 1. Using varied length of a coated sample channel to modify EOF in a separation channel
2. Using a restriction to reduce EOF in a sample channel

TABLE 5

V. Modification Of Electrokinetic Vector Mobility/Analyte Affinity To Induce Orthogonal Analyte Stacking/Injection A. Sample matrix modifications 1. Inclusion of continuous background electrolyte to maintain equivalent conductivity
2. Inclusion of continuous background electrolyte to maintain higher conductivity
3. Inclusion of a second, high-mobility co-ion in the sample matrix B. Separation buffer modifications 1. Addition of organic modifier to enhance access of analytes to micelle
2. Increase of the background electrolyte to induce isotachophoretic effects

TABLE 6

VI. Description Of Novel Electrokinetic Vectors For Modifying Analyte Mobility To Induce Orthogonal Analyte Stacking/Injection A. Electrokinetic vector can include a neutral species that affects the electrophoretic mobility of a charged species, such as an entanglement matrix.

Still referring to Tables 1–6, provided immediately below are exemplary applications to the outlined conditions.

Table 1.I.A.1: A capillary or microchannel known to those skilled in the art is filled with a separation buffer containing an anionic electrokinetic vector such as described in the "Examples" section of this instant disclosure, e.g., sodium dodecyl sulfate or sodium cholate. Typical concentration is about 5–300 mM. A buffering agent such as sodium borate or sodium phosphate ($Na_2HPO_4$, $NaH_2PO4$, $H_3PO4$), or Tris/TRIZMA, or combinations thereof or other buffering agents to obtain a pH that allows the formation of electroosmotic flow under an applied electric field is used. A sample matrix without the electrokinetic vector is prepared with either the same buffering agent as found in the separation buffer, or a different salt such as sodium chloride or other salt to maintain a similar or higher conductivity than the separation buffer. The sample matrix may also comprise a biological or other sample containing a native salt concentration, which may be used "as is" or augmented with an appropriate salt or buffer to allow the formation of a stacking boundary necessary to allow subsequent electrokinetic stacking. The sample matrix may also contain a combination of a buffering agent and a higher-mobility co-ion such as phosphate, sulfate, charged cyclodextrins, fluoride, chloride, bromide, or iodide or other high-mobility co-ions. Neutral analytes of interest are dissolved in the sample matrix.

Injection is performed by subjecting the inlet end of the capillary in contact with the sample matrix and the outlet end of the capillary in contact with the separation buffer. The inlet end of the capillary contains the anode, the outlet end of the capillary contains the cathode. An electric field is applied, typically but not exclusively between about 10 and 1000 volts per centimeter. This causes the injection of neutral analytes by electroosmotic flow (EOF) into the capillary. Simultaneously, the anionic electrokinetic vector in the separation buffer forms a boundary with the sample matrix co-ion(s), and the solvent in the sample matrix passes through the boundary as the solvent moves toward the cathode (outlet). A typical injection can allow more than 5 capillary volumes of sample matrix to be introduced into the capillary (See Palmer etal. Analytical Chemistry 2001). Injection is terminated by ceasing the electric field, removing the sample matrix from contact with the capillary inlet, and placing separation buffer and the anode at the capillary inlet. An electric field is again applied, typically between about 10 and 1000 volts per centimeter, to allow the subsequent separation and detection of the neutral analytes.

Table 1.I.A.2: These same conditions (1.I.A.1) can be used to stack and detect cationic analytes dissolved in the sample matrix.

Table 1.I.A.3: These same conditions (1.I.A.1) can be used to stack and detect cationic analytes, in this case, with an uncharged (neutral) or zwitterionic electrokinetic vector in the separation buffer instead of an anionic electrokinetic vector.

Table 1.I.B.1: A typical capillary or microchannel is filled with a separation buffer containing cationic electrokinetic vector. Typical concentration is about 5–300 mM. A buffering agent such as sodium borate or sodium phosphate ($Na_2HPO_4$, $NaH_2PO4$, $H_3PO4$), or Tris/TRIZMA, or combinations thereof or other buffering agents or proprietary compounds to obtain conditions that allow for reversed electroosmotic flow under an applied electric field is used. A sample matrix without the electrokinetic vector is prepared with either the same buffering agent as found in the separation buffer, or a different salt such as sodium chloride or other salt to maintain a similar or higher conductivity than the separation buffer. The sample matrix may also comprise of a biological or other sample containing a native salt concentration, which may be used "as is" or augmented with an appropriate salt or buffer to allow the formation of a stacking boundary necessary to allow subsequent electrokinetic stacking. The sample matrix may also contain a combination of a buffering agent and a higher-mobility co-ion such as lithium, sodium, potassium, charged cyclodextrins, or other high-mobility co-ions. Neutral analytes of interest are dissolved in the sample matrix.

Injection is performed by subjecting the inlet end of the capillary in contact with the sample matrix and the outlet end of the capillary in contact with the separation buffer. The inlet end of the capillary contains the cathode, the outlet end of the capillary contains the anode. An electric field is applied, typically but not exclusively between about 10 and 1000 volts per centimeter. This causes the injection of neutral analytes by reversed electroosmotic flow into the capillary. Simultaneously, the cationic electrokinetic vector in the separation buffer forms, a boundary with the sample matrix co-ion(s), and the solvent in the sample matrix passes through the boundary as the solvent moves toward the anode (outlet). Injection is terminated by ceasing the electric field, removing the sample matrix from contact with the capillary inlet, and placing separation buffer and the cathode at the capillary inlet. An electric field is again applied, typically between about 10 and 1000 volts per centimeter, to allow the subsequent separation and detection of the neutral analytes.

Table 1.I.B.2: These same conditions (1.I.B.1) can be used to stack and detect anionic analytes dissolved in the sample matrix.

Table 1.I.B.3: These same conditions (1.I.B.1) can be used to stack and detect anionic analytes, in this case, with an uncharged (neutral) or zwitterionic electrokinetic vector in the separation buffer instead of a cationic electrokinetic vector.

Table 2.II.A.1: The same conditions as found in (1.I.A.1) can be used with the injection vector, electroosmotic flow, augmented by applying positive pressure, typically but not exclusively about 1 to 500 mbar above atmospheric pressure, at the inlet during the electrokinetic injection step.

Table 2.II.A.2: The same conditions as found in (1.I.A.2) can be used with the injection vector, electroosmotic flow, augmented by applying positive pressure, typically but not exclusively about 1 to 500 mbar above atmospheric pressure, at the inlet during the electrokinetic injection step.

Table 2.II.A.3: The same conditions as found in (1.I.A.3) can be used with the injection vector, electroosmotic flow, augmented by applying positive pressure, typically but not exclusively about 1 to 500 mbar above atmospheric pressure, at the inlet during the electrokinetic injection step.

Table 2.II.B.1: The same conditions as found in (1.I.B.1) can be used with the injection vector, electroosmotic flow, augmented by applying positive pressure, typically but not exclusively about 1 to 500 mbar above atmospheric pressure, at the inlet during the electrokinetic injection step.

Table 2.II.B.2: The same conditions as found in (1.I.B.2) can be used with the injection vector, electroosmotic flow, augmented by applying positive pressure, typically but not exclusively about 1 to 500 mbar above atmospheric pressure, at the inlet during the electrokinetic injection step.

Table 2.II.B.3: The same conditions as found in (1.I.B.3) can be used with the injection vector, electroosmotic flow, augmented by applying positive pressure, typically but not exclusively about 1 to 500 mbar above atmospheric pressure, at the inlet during the electrokinetic injection step.

Table 2.II.C.1: The same conditions as found in (1I.A.1) can be used with the injection vector, electroosmotic flow, augmented by applying negative pressure, typically but not exclusively about 1 to 500 mbar above atmospheric pressure, at the outlet during the electrokinetic injection step.

Table 2.II.C.2: The same conditions as found in (1.I.A.2) can be used with the injection vector, electroosmotic flow, augmented by applying negative pressure, typically but not exclusively about 1 to 500 mbar above atmospheric pressure, at the outlet during the electrokinetic injection step.

Table 2.II.C.3: The same conditions as found in (1I.A.3) can be used with the injection vector, electroosmotic flow, augmented by applying negative pressure, typically but not exclusively about 1 to 500 mbar above atmospheric pressure, at the outlet during the electrokinetic injection step.

Table 2.II.D.1: The same conditions as found in (1.I.B.1) can be used with the injection vector, electroosmotic flow, augmented by applying negative pressure, typically but not exclusively about 1 to 500 mbar above atmospheric pressure, at the outlet during the electrokinetic injection step.

Table 2.II.D.2: The same conditions as found in (1.I.B.2) can be used with the injection vector, electroosmotic flow, augmented by applying negative pressure, typically but not exclusively about 1 to 500 mbar above atmospheric pressure, at the outlet during the electrokinetic injection step.

Table 2.II.D.3: The same conditions as found in (1.I.B.3) can be used with the injection vector, electroosmotic flow, augmented by applying negative pressure, typically but not exclusively about 1 to 500 mbar above atmospheric pressure, at the outlet during the electrokinetic injection step.

Table 3.III.A.1: The same conditions as found in (2.II.A.1) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.A.2: The same conditions as found in (2.II.A.2) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.A.3: The same conditions as found in (2.II.A.3) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.B.1: The same conditions as found in (2.II.B.1) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.B.2: The same conditions as found in (2.II.B.2) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.B.3: The same conditions as found in (2.II.B.3) can be used in an absence of or reduced electroosmotic flow with the injection vector provided by applying positive pressure, typically but not exclusively about 1 to 500 mbar above atmospheric pressure, at the inlet during the electrokinetic injection step.

Table 3.III.C.1: The same conditions as found in (2.II.C.1) can be used in an absence of or reduced electroosmotic flow with the injection vector provided by applying negative pressure, typically but not exclusively about 1 to 500 mbar above atmospheric pressure, at the outlet during the electrokinetic injection step.

Table 3.III.C.2: The same conditions as found in (2.II.C.2) can be used in an absence of or reduced electroosmotic flow with the injection vector provided by applying negative pressure, typically but not exclusively about 1 to 500 mbar above atmospheric pressure, at the outlet during the electrokinetic injection step.

Table 3.III.C.3: The same conditions as found in (2.II.C.3) can be used in an absence of or reduced electroosmotic flow with the injection vector provided by applying negative pressure, typically but not exclusively about 1 to 500 mbar above atmospheric pressure, at the outlet during the electrokinetic injection step.

Table 3.III.D.1: The same conditions as found in (2.II.D.1) can be used in an absence of or reduced electroosmotic flow with the injection vector provided by applying negative pressure, typically but not exclusively about 1 to 500 mbar above atmospheric pressure, at the outlet during the electrokinetic injection step.

Table 3.III.D.2: The same conditions as found in (2.II.D.2) can be used in an absence of or reduced electroosmotic flow with the injection vector provided by applying negative pressure, typically but not exclusively about 1 to 500 mbar above atmospheric pressure, at the outlet during the electrokinetic injection step.

Table 3.III.D.3: The same conditions as found in (2.II.D.3) can be used in an absence of or reduced electroosmotic flow with the injection vector provided by applying negative pressure, typically but not exclusively about 1 to 500 mbar above atmospheric pressure, at the outlet during the electrokinetic injection step.

Experimental Results

The following examples are offered as being illustrative of exemplary embodiments of the present invention. These examples are non-limiting and are offered as exemplary only.

EXAMPLE NO. 1

Mode for Carrying Out the Experiment—Example No. 1

With regards to the materials, HPLC-grade water (Fisher Company, St. Louis, Mo.) was used for all separation buffers and sample matrixes. Sodium tetraborate, sodium hydroxide, sodium chloride, and punctilious ethanol were obtained from Sigma Company (St. Louis, Mo.). Cholic acid, sodium salt hydrate, was obtained from Aldrich Chemical Company (Milwaukee, Wis.). Corticosteroids were obtained from Steraloids, Inc. (Newport, R.I.). BODIPY (4,4-difluoro-5,7-dimethyl-4-bora-3a,4a-diaza-s-indacene-3-propanol) was obtained from Molecular Probes Company(Eugene, Oreg.), and sodium fluorescein was obtained from Acros Company, New Jersey. Sodium dodecyl sulfate was obtained from Bio-Rad Laboratories (Hercules, Calif.).

With respect to the capillary electrophoresis, experiments with corticosteroid analytes were conducted with a Hewlett Packard HP 3D-CE instrument interfaced with a Hewlett Packard Kayak XA computer with HP 3D-CE ChemStation Rev. A.06.01[403] software for control of the instrument and data collection. The capillaries were 19, 27, or 50 µm i.d., as indicated, bare silica, polyimid surfaced, ~370 µm o.d., from Polymicro Technologies, Incorporated (Phoenix, Ariz.). The electrokinetic injection and separation polarities were normal (anode at the inlet). Capillary temperature was maintained at 20° C. and detection was by UV absorption at 242 nm with a 20 nm bandwidth except as noted. Stacking of a fluorescent neutral compound (BODIPY) was performed with a Beckman P/ACE 5510 using a P/ACE system laser module 488 equipped with a 27 µm by 37 cm capillary.

With regards to the separation buffer and sample matrix preparation, the separation buffer vial volumes were 0.7 ml. The sample matrix volumes were 100 µl. The separation buffer consisted of 80 mM sodium cholate, 5 mM tetraborate, and 10% punctilious ethanol in HPLC-grade water (pH range 8.9–9.1), or sodium dodecyl sulfate, at concentrations as noted, with 5 mM tetraborate and 20% methanol. Separation buffers were degassed by manual decompression in a syringe and passed through a 0.2 µm pore-diameter filter before use. Sample matrixes were prepared with sodium chloride or sodium tetraborate at stated concentrations in HPLC-grade water. Crystalline corticosteroids were dissolved in punctilious ethanol at 1.00 µM (316 to 362 µg/ml). Aliquots were dried down and re-suspended at stated dilutions. Standards were stored at 4° C. when not in use. Analyte concentrations in the sample matrixes were as stated in each experiment.

With regards to the capillary electrophoresis conditions, the capillary length was 33 or 48.5 cm with an i.d. of 50 µm except as noted. New capillaries were conditioned by flushing with 1.0 M sodium hydroxide, water, and separation buffer, in order. The same procedure was used to flush the capillaries at the start of each day's experiments. For separations, the capillary was first flushed by high pressure (~950 mbar) with a three- to five-capillary volume of fresh separation buffer (1–5 min). Separations were carried out at 30 kV. The separation buffer was replaced after no more than two hours total running time and the capillaries were reconditioned daily by flushing with 1.0 M sodium hydroxide and water.

With respect to the sample matrix and sample injection conditions, the velocity of sample plug injection by low-pressure and electrokinetic injection was determined for 33 cm capillaries with i.d.'s of 19, 27, and 50 µm using 150 mM sodium chloride sample matrix, and 80 mM sodium cholate with 10% ethanol and 40 mM borate separation buffer (pH ~9). Triplicate injections were made under reverse pressure (−50 mbar) or reverse voltage (−30 kV) from the outlet (sic) vial, which contained the high-salt matrix. During injection, time of absorbance shift at the detection point under these reversed conditions (distance 8.5 cm) was recorded to determine injection velocity. Injection velocity was similarly obtained with sample matrixes and separation buffer used for sweeping experiments (50 mM borate sample matrix and 40 mM sodium dodecyl sulfate with 20% methanol and 20 mM borate as separation buffer, pH~9). Viscosity differences between the sample matrixes and the separation buffer did not affect accurate determination of injection plug length. Relative conductivity of solutions was gauged as previously described in Palmer, J., Munro, N. J., Landers, J. P. "*A universal Concept for Stacking Neutral Analytes in Micellar Capillary Electrophoresis*", Anal. Chem. 1999, 71, 1679–87.

With the 50 µm×33 cm capillary, sample matrixes consisting of 0, 25, 50, 75, 100, 150, 200 and 300 mM sodium chloride were examined for stacking effect by electrokinetic injections at 30 kV for 40 seconds. With the optimal salt concentration for stacking (150 mM sodium chloride), 5, 10, 20, 40, and 80 second injections were examined to verify linearity of injection time with peak response of neutral analytes at the detector. Peak area was examined to determine linearity of analyte injection with injection duration. Triplicate electrokinetic injections from six identical high-salt samples, with separation mode using a single set of separation buffer vials were utilized to determine the robustness of the separation buffer. Eighteen injections from a single high-salt sample matrix vial using a single set of separation buffer vials, were undertaken to determine the reproducibility of the high-salt electrokinetic injection mode. Peak height, area, and migration times were examined. Continuous conditions were examined with sample matrixes with conductivity equal to the separation buffer, with electrolyte conductivity in the sample matrix adjusted by addition of the separation buffer background electrolyte (borate), to provide continuous electrophoretic conditions. Sample matrix pH was previously determined to be unimportant with the selected analytes. Stacking of a fluorescent neutral compound (BODIPY) was demonstrated on the capillary format with conditions described above. Buffer and sample preparation were as listed for the corticosteroid separations, with BODIPY at 67 nM in 150 mM sodium chloride.

With respect to the electrokinetic stacking conditions on the microchip, a simple T-configuration cross-channel injection microchip (Alberta Microelectronics Corporation, Edmonton, Alberta, Canada) was utilized to demonstrate stacking of a neutral analyte on a microchip format. The separation channel was 7.6 cm from the junction of the sample cross channel to the outlet (O), with a hemispherical cross section 50 µm wide by 20 µm deep. The sample T-channel had the same cross-section dimensions as the separation channel, extending perpendicular to the separation channel for 0.6 cm to the sample well (S) and waste well (W). The microchip channels were conditioned by flushing with 1.0 M sodium hydroxide, water, and separation buffer, in order. The apparatus for pressure-flushing the microchip channels was previously described in copending U.S. application Ser. No. 09/418,659 by Palmer et al. For analyses, the sample well was flushed with 150 mM sodium chloride, then filled with the sample matrix consisting of 150 mM sodium chloride with BODIPY at 67 nM. Wells I, O, and W were filled to equivalent levels with separation buffer. The separation channel was conditioned by inducing a field between I and O (+500/−2000) for 100 seconds while holding S and W at ground to reduce cross-channel leakage. Electrokinetic injection was performed by applying an electric field between S and O (+250/−1000) for 20, 40 60, 80, 100 and 120 seconds, while floating W and I. Identical injections with BODIPY at 134 nM dissolved in separation buffer were made to demonstrate non-stacking injection conditions. Separation mode was initiated by re-directing the electric field from I to O (+500/−2000), with S and W at ground. Detection was by laser-induced fluorescence. An argon ion laser (488 nm) was focused by a microscope objective (60×) into the separation channel. Fluorescence (514 nm) was collected co-linearly through the microscope objective, focused through a lens (15.6 cm focal length, plano-convex), and passed through a spatial filter (0.3 mm pinhole) and a bandpass filter to a photo multiplier tube detector.

Results and Discussion—Example No. 1

Effect of Varied Sample Matrix Salt Concentration on Stacking Efficiency. As graphically represented in FIG. 4, using different concentrations of sodium chloride (a high-mobility co-ion) in the sample matrix, electrokinetic injections of corticosteroids (model neutral analytes) in sample matrixes ranging from 0 to 300 mM NaCl were examined. These experiments examined the effect of the leading co-ion (chloride) on inducing stacking conditions for the electrokinetic vector, cholate. For sample matrixes with conductivity below that of the separation buffer (0 and 25 mM sodium chloride) no evidence of sample stacking is apparent. Increasing the sodium chloride concentration to 50 mM yields a sample matrix that has roughly the same conductivity as the separation buffer, yet negligible analyte stacking is observed. When the conductivity of the sample matrix is made to exceed that of the separation buffer by increasing the sodium chloride concentration to about 75 mM or higher, analyte stacking is observed.

Figure 4:
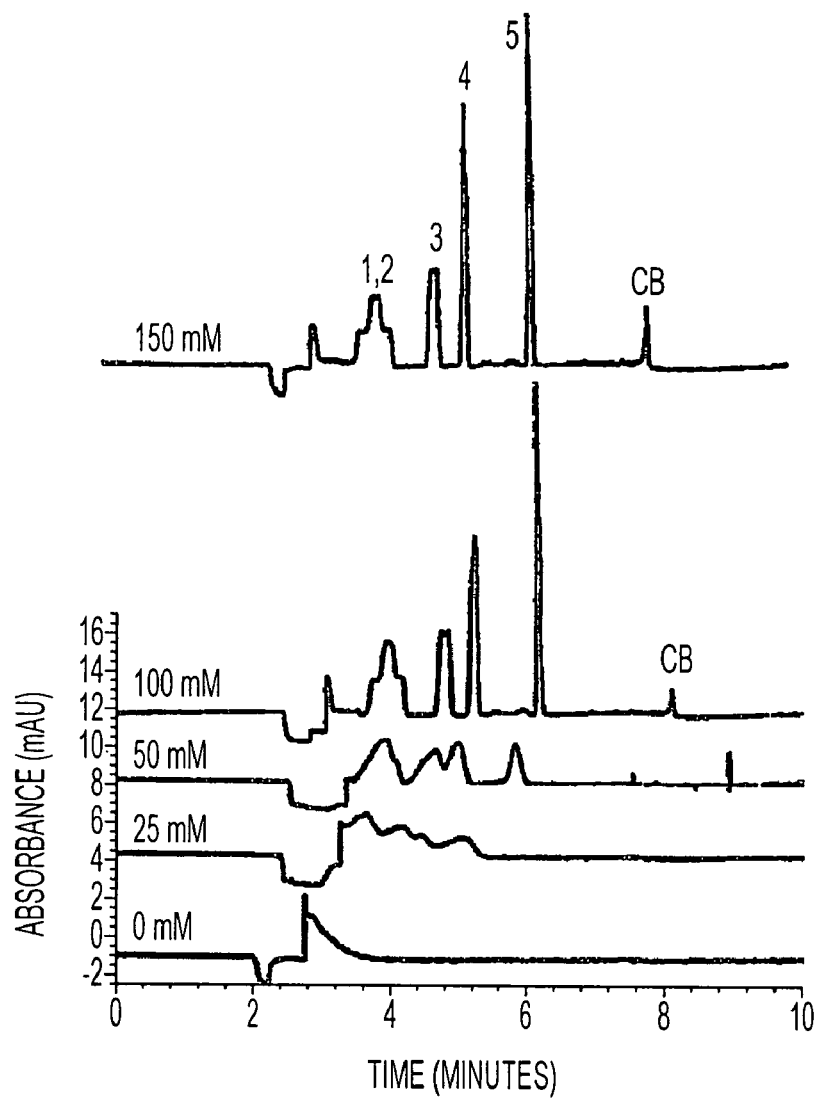
FIG. 4. shows an electropherogram with absorbance (mAU) plotted versus time and demonstrates the extent to which stacking occurs at different sample matrix salt concentrations. The sample matrix sodium chloride concentrations are as listed in the figure, and the injections are at 30 kV for 40 seconds. Separation conditions are as follows: 80 mM sodium cholate, 10% ethanol, 5 mM tetraborate, pH ~9 separation buffer. The capillary is 50 μm (i.d.) by 48.5 cm. Separation is carried out at 30 kV and the separation buffer was roughly the same conductivity as the 50 mM sodium chloride sample matrix. Peak order for 1–5 included the following: cortisone, cortisol, 11-deoxycortisol, 17-hydroxyprogesterone, and progesterone.

As shown in FIG. 4, it is demonstrated that the stacking efficiency in this mode is dependent on the concentration of salt in the sample matrix. The co-ion in the sample matrix (chloride in this case) must be present at a concentration sufficient to reduce its velocity to less than that of the electrokinetic vector in the separation buffer. This causes the formation of a pseudo-steady state field boundary that forces an increased concentration of the electrokinetic vector in the separation buffer at the cathode-side of the co-ion boundary. Under continuous conditions where the conductivity of the sample matrix and separation buffer differs, a "soft boundary" between zones of different conductivity can occur. A soft boundary is caused by differences in the zonal electroosmotic flow intrinsic mobilities that form a pressure barrier, leading to a Pousieulle-flow profile that detracts from the stacking effect of analytes encountering the boundary.

However, under electrophoresis with discontinuous conditions, it is unlikely a separation buffer co-ion with a lower anodic mobility than the sample matrix co-ion could overtake the higher-mobility sample matrix co-ion in the direction of the anode. Hence, a stock-straight interface is exhibited between the sample matrix co-ion and the separation buffer co-ion when the co-ion in the sample matrix induces a pseudo-steady state boundary. For the unique case here in which the leading electrolyte is electrokinetically injected adjacent to the separation buffer containing the trailing electrolyte (the electrokinetic vector), a pseudo-steady state co-ion boundary will be formed under the following conditions. See Palmer, J., Landers, J. P, "*Stacking Neutral Analytes in Capillary Electrokinetic Chromatography with High Salt Sample Matrixes*", Anal. Chem. 2000, 72, 1941–1943:

$$\mu_S^* E_S < \mu_{ev}^* E_{ev} \quad (11)$$

with the restriction that:

$$\mu_S > \mu_{ev} \quad (12)$$

where $\mu_S$ and $\mu_{ev}$ are the electrophoretic mobility of the co-ion in the sample matrix and separation buffer, respectively, and $E_S$ and $E_v$ are the electric field strengths in the sample co-ion zone and the electrokinetic vector zone. This is consistent with chloride having a postulated intrinsic mobility of roughly 1.5–3 times that of the cholate micelle under these conditions. This is based on the necessity of supplying chloride ion in the sample matrix at a concentration of 1.5–3 times that of the electrokinetic vector in the separation buffer for stacking to occur. Absolute mobility is difficult to interpret due to variations in ionic constituents that induce ITP effects as well as field differences induced by zonal conductivity differences.

Effect of Electrokinetic Injection Length on Detection. The velocities of electrokinetic and low-pressure injected sample matrix plugs over a range of capillary i.d. and lengths were compared. The time at which neutral components of the sample matrix (e.g., water or organic modifier) reached the detection point with 50 mbar pressure or 30 kV injection was used to determine velocity of respective injections. The sample plug length for neutral analytes can be determined by multiplying the pressure-induced flow velocity by duration of pressure injection, and by multiplying the electroosmotic flow velocity by duration of electrokinetic injection. With the sample and separation buffer conditions described above, a 33 cm by 50 µm i.d. capillary has a low-pressure injection velocity of 0.081 cm per second, or an electroosmotic flow injection velocity of 0.372 cm per second (with an applied voltage of 30 kV). Electrokinetic injection is 4.6 times faster at this capillary length and internal diameter. However, a 33 cm capillary with an i.d. of 19 µm has a low-pressure injection velocity of 0.012 cm per second, or an electroosmotic flow injection velocity of 0.295 cm per second, representing an injection rate 25-times faster when utilizing electroosmotic flow. With longer capillaries, low-pressure injection is slowed by an increase in flow resistance proportional to the capillary length. Likewise with electrokinetic injection, the field is reduced proportional to capillary length.

Linearity of peak area to injection length was examined to determine whether equation (3) could be corroborated by experimental data. With the 50 µm i.d. by 33 cm capillary, peak area for progesterone is linear with electrokinetic injection lengths ($R^2$=0.9873), from 5 to 80 seconds (125% of the effective capillary length, i.e., 80 second electrokinetic injection, capillary length to detector, 24.5 cm, injected plug length, 30 cm). Similar analysis was undertaken with 50 µm i.d. capillaries of 48.5 and 64.5 cm length, with peak areas corresponding to injection times by 0.9979<$R^2$<0.9799, with no trending differences. The linearity of peak area with injection duration indicates that the amount of neutral analyte injected is linear with injection duration, and that equation (3) holds for predicting the amount of neutral analyte injected via electroosmotic flow with high-salt sample matrixes. There appears to be no bias due to the bulk electroosmotic flow changing as a function of sample plug length. Further study is ongoing to understand this effect.

The total analysis times for electrokinetic versus pressure injection of long sample plugs can be compared by summing the injection and analysis times. With a 50% capillary-length injection using high-salt sample matrixes and a 33 cm×50 µm capillary, electrokinetic injection is approximately 50% faster (ca. 2.5 minute total analysis versus ca. 3.5 minutes with pressure injection). However, with smaller i.d. capillaries, total analysis times can be decreased by roughly an order of magnitude with the use of electrokinetic injection. For example, an 80% effective capillary length injection takes 1808 seconds by low-pressure injection with a 33 cm×19 µm capillary. The same injection can be made by a 73 second electrokinetic injection at 30 kV. With separation times of approximately 150 seconds in either case, the total analysis time with electrokinetic injection is approximately 9 times faster (FIG. 3). For electrokinetic injection with a stacking boundary that is moving against the electroosmotic flow, capillary injections of more than 100% of the effective capillary length can be made (FIG. 1), with capillary length still remaining for separation of the stacked analytes. Likewise, with continuous conditions an electrokinetic injection length 170% of the effective capillary length (~42 cm sample plug length with an effective capillary length of 24.5 cm) can be made. The resulting resolution is similar to that observed when using a pressure injection of ~30 cm with a capillary length of 80.5 cm with capillaries of 50 µm i.d. It is possible to use a longer capillary to increase the injected plug length, as well as to increase the effective capillary length remaining for separation. However, reduction in the maximum electric field is proportional to the length of the capillary, and analysis and injection times are proportionally longer, as well. In addition, a better signal-to-noise ratio is observed with electrokinetic injection, and analysis time with a 50 µm i.d. capillary is reduced from ca. 2000 seconds with a 42 cm sample plug in an 80.5 cm long capillary to ca. 200 seconds with a 33 cm capillary (FIG. 3).

Figure 5:
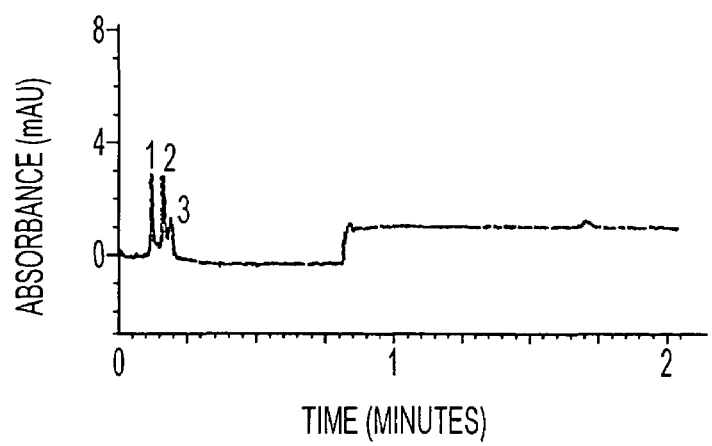
FIG. 5. is an electropherogram showing absorbance (mAU) plotted versus time for electrokinetic stacking injection with continuous buffer conditions. Sample matrix was 50 mM borate (approximately the same conductivity of the separation buffer). The parameters are: cortisone, 11-deoxycortisol, and progesterone at 10 ng/ml. The separation buffer comprises: 50 mM SDS, 20% methanol, 5 mM tetraborate, pH ~9. 50 μm i.d. by 33 cm capillary, and separation at 30 kV.
Figure 6:
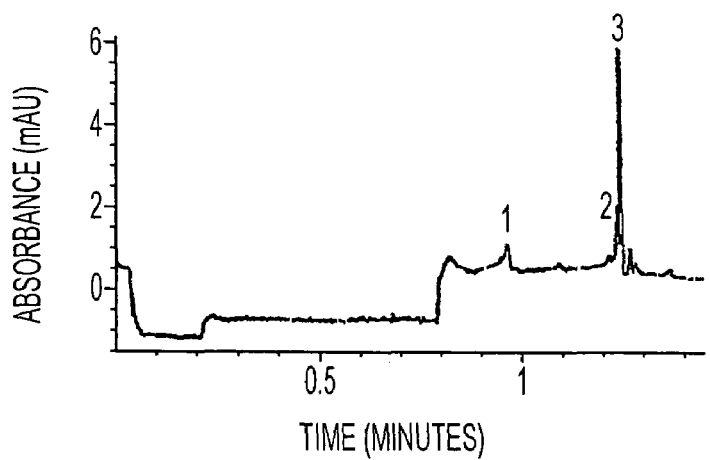
FIG. 6. an electropherogram showing a graphical representation (absorbance versus time) for electrokinetic stacking injection instigated by a leading co-ion. Sample matrix was 20 mM borate with 4 mM hydrogen phosphate, pH ~9, cortisone, 11-deoxycortisol, and progesterone analytes at 50 ng/ml, with 30 kV injection for 60 seconds. Separation conditions and peak order as in FIG. 5.

Limits of Detection with Electrokinetic Stacking Injections. With electrokinetic injection, extremely long, fast sample injections can be made. Since the stacking process occurs at a co-ion boundary that moves into the capillary at a lower velocity than the electroosmotic flow, it is possible to inject sample plugs longer than the effective length of the capillary. As can be seen (FIG. 5), the UV absorption signal of the electroosmotic flow at the detector immediately after the initiation of separation shows that the injection was approximately 100% of the effective capillary length (i.e., the electroosmotic flow-injected plug was electrokinetically injected nearly to the detector window). High-k analyte/micelle systems are particularly well suited to this type of extended injection. In this case, sodium dodecyl sulfate was utilized as the electrokinetic vector for corticosteroid analytes. The sample matrix was 10 mM tetraborate with a leading co-ion hydrogen phosphate at 5 mM. Electrokinetic injection at 30 kV was made for 60 seconds directly from the sample vial. Separation was carried out at 30 kV. Three corticosteroids are resolved in less than two minutes at 50 ng/ml. While the signal to noise with electrokinetic injection under sweeping conditions (FIG. 5) is similar to that already reported, the results (FIG. 6) show approximately an order of magnitude better detection for the progesterone peak, with a theoretical plate number of 2,000,000 per meter. The 11-deoxycorticosterone exhibited a plate number of 1,100,000 per meter, while the cortisone peak is not as well sharpened. This stacking mechanism is thus approximately an order of magnitude more sensitive, as well as an order of magnitude faster than that previously reported in the presence of conventional electroosmotic flow.

Reproducibility for Electrokinetic Stacking Injections. To determine the reproducibility of the electrokinetic injection method, the robustness of both the sample matrix and separation buffer was examined by repeated injection from a single sample matrix vial (n=18) and triplicate separation cycles with injections from six identical high-salt sample matrix vials (n=18). Peak height, peak area, and migration time for three analytes were examined. With injections from three separate identical high-salt sample matrixes, using a single set of separation buffer vials, analyte migration times have a coefficient of variance (CV) of 0.2%, peak heights between 3.2 and 3.9%, and peak areas between 6.4 and 8.2%. It is notable that the separation buffer is not affected by repeated high-salt sample matrix injections.

Repeated injections from a single high-salt sample vial show migration time CV values of 0.2–0.3% for up to 18 injections (all that were attempted), with CV values for peak height and area comparable for up to ten injections. For more than ten injections, a trend of decreasing peak height and area is observed. Hydrolysis of the sample matrix can be severe with low-ionic strength sample matrixes, limiting sampling from a single vial to one electrokinetic injection. However, it has been clearly shown that multiple injections can be made from high salt sample matrixes with extremely reproducible analyte responses, thus expanding the utility of high-salt matrixes in this mode.

Figure 7:
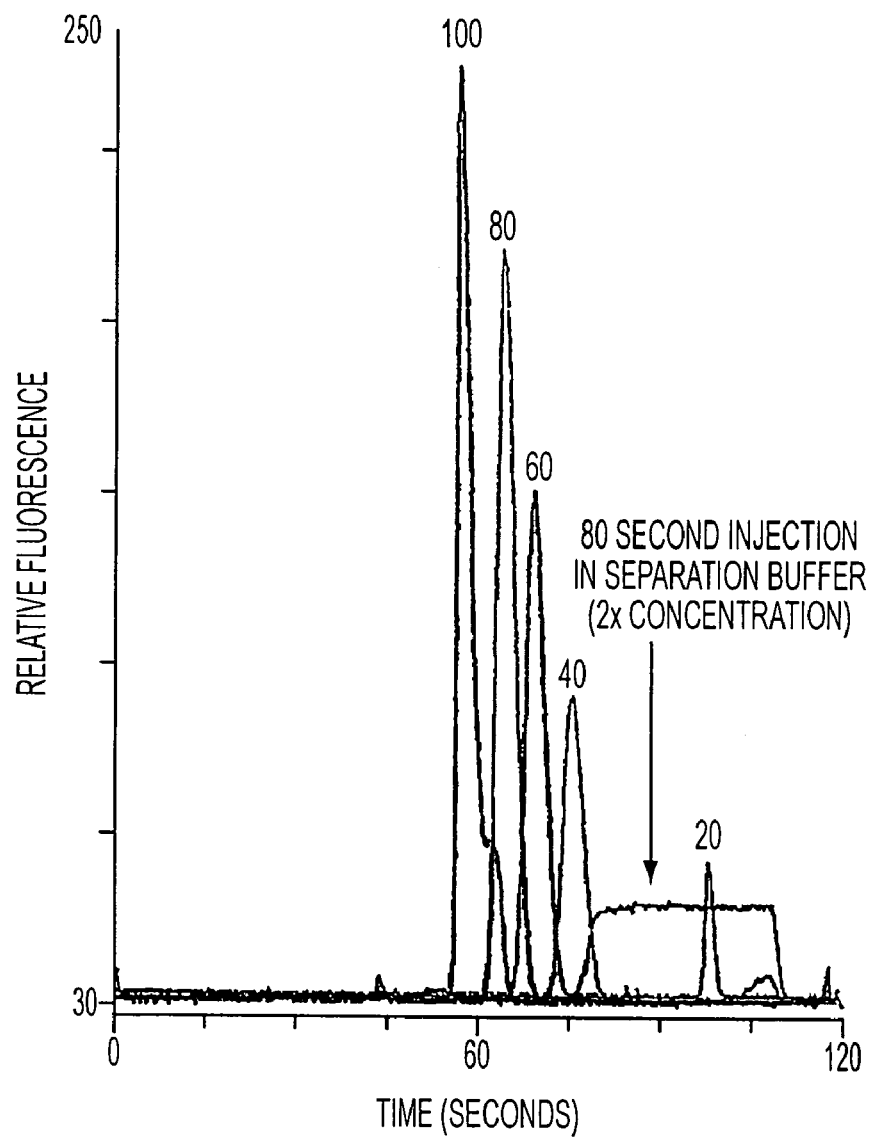
FIG. 7 is an electropherogram showing relative fluorescence versus time for electrokinetic stacking injection on a microchip. Sample matrix was 150 mM sodium chloride. 4,4-difluoro-5,7-dimethyl-4-bora-3α,4α-diaza-s-indacene-3-propanol (BODIPY) was used as the analyte at 67 nM. Injection was carried out at 183 V/cm for the duration of time shown in the figure. Separation conditions: 80 mM sodium cholate, 10% ethanol, 5 mM tetraborate, pH ~9 run buffer, separation at 366 V/cm. Further conditions include 80 second injection of 134 nM BODIPY in separation buffer included to show non-stacking injection. An exemplary layout, but not limited thereto, may include the microchip layout as shown in FIG. 9, with reservoirs S, sample, I, inlet, W, waste, and O outlet.
Figure 8:
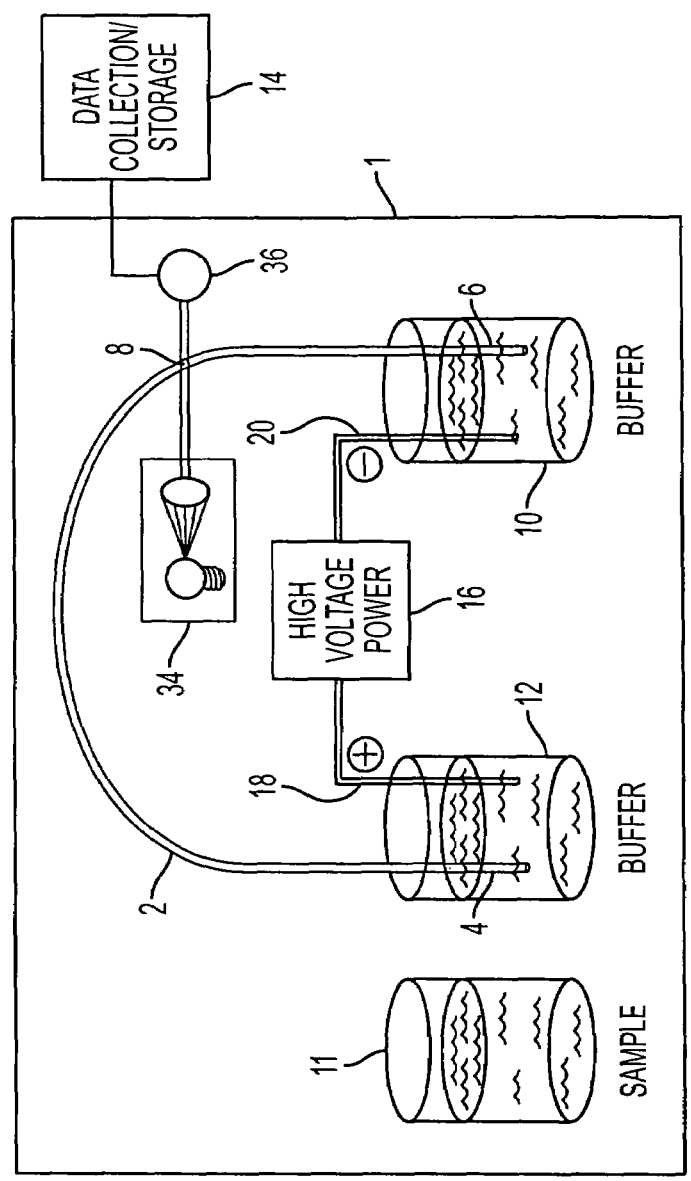
FIG. 8 is a schematic representation of an exemplary test set-up used to practice the present invention.
Figure 9:
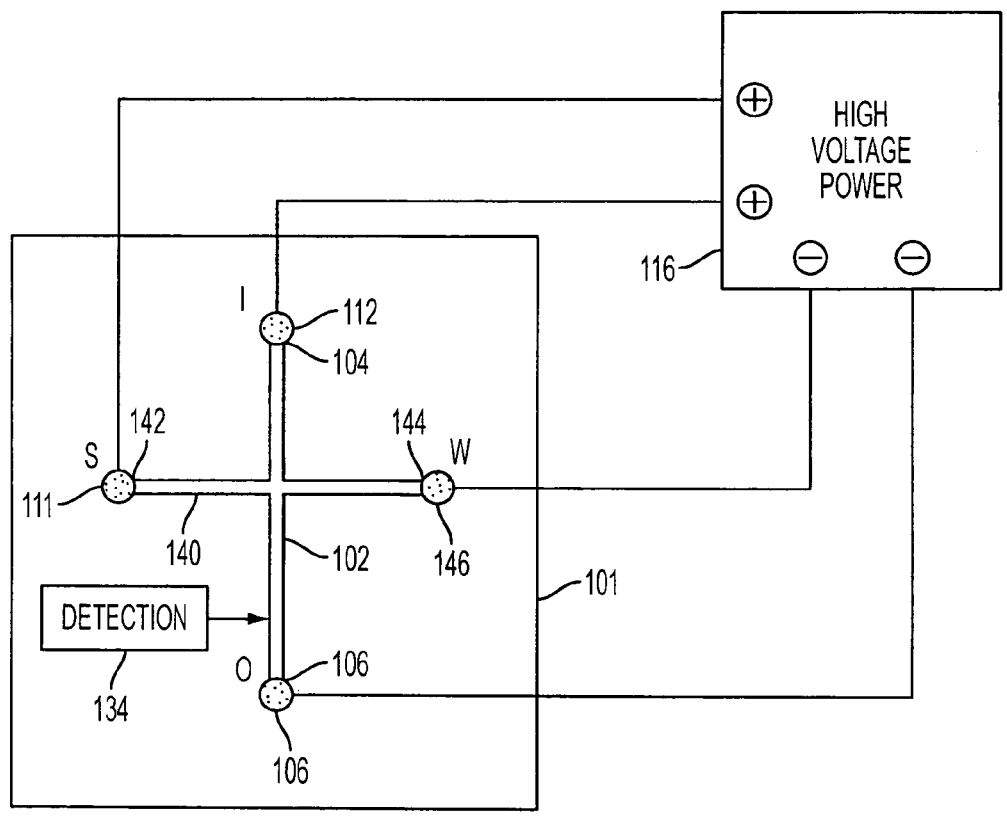
FIG. 9 is a schematic representation of an exemplary test set-up used to practice the present invention, wherein electrophoretic unit is a T-configuration cross-channel microchip.

Electrokinetic Stacking Injections on a Microchip. Field-amplified stacking of charged analytes on a microchip has been previously demonstrated. Since UV detection is difficult to accomplish on the microchip, the demonstration of high-salt electrokinetic stacking injection on a microchip will have to exploit neutral, fluorescent analytes that can be excited by an argon ion laser. Consequently, BODIPY, a neutral and fluorescent analyte, was utilized to demonstrate stacking on a microchip. As shown in FIG. 9, using a simple T-configuration cross-channel injection microchip, it was possible to emulate the electrokinetic injection method used on the capillary format by placing the separation buffer in the inlet (I), outlet (O), and waste (W) wells, and the high-salt sample matrix in the sample well (S). By applying an electric field from the sample well to the outlet, electrokinetic injection of the high-salt sample matrix was initiated. Electrokinetic injection sample stacking was terminated and the subsequent separation initiated by applying voltage between the inlet and the outlet. Electrokinetic injections from 20 to 120 seconds were carried out to determine if visual evidence in support of stacking could be observed. For comparison to non-stacking injections, the analyte was dissolved in the separation buffer and injected for 20 to 120 seconds, with the 80 second injection shown (note the control had twice the initial concentration of analyte as used in the stacking experiments) (FIG. 7). The injection field was 50% that of the separation field. The linear increase in analyte peak height with injection time is clear evidence that the stacking of the neutral analyte is occurring. Note the 100 second injection has a fluorescence response approximately 10-times greater than the analyte injected in separation buffer (non-stacking injection). Similarly, the non-stacking conditions had twice the concentration of BODIPY, hence, a 20-fold peak height improvement is evidenced by utilizing a high-salt stacking injection.

Conclusion—Example No. 1

The electrokinetic stacking of neutral analytes driven by electroosmotic flow for subsequent EKC separation has been demonstrated. With discontinuous sample matrix/separation buffer co-ions, (high-salt sample matrix mode), or continuous sample matrix/separation buffer co-ions (sweeping), neutral analytes can be injected at the velocity of the electroosmotic flow. The stacking boundary in each mode allows electrokinetic sample plug injections greater than the actual capillary length. Not only was a marked increase in the subsequent resolution of analytes at injection lengths required for low detection limits of neutral analytes possible, injection times were reduced by 4- to 50-fold versus pressure injections. Injection of neutral analytes by electroosmotic flow is a logical, broadly applicable, and expedient stacking method for EKC. Electrokinetic injection has the potential to provide a convenient mode for stacking injections with capillary arrays, and might also be exportable to other methods that utilize electrophoretically-active stacking junctions, such as pH-mediated stacking. In addition, the use of electrokinetic injection allows the translation of neutral analyte stacking in high-salt samples from the capillary to the microchip format. Many methods for gating injections in the microchip format have been devised. In this case, a chemical boundary is used to maintain an interface between the sample matrix and separation buffer during injection. When sample matrix parameters are correctly instituted, the generation of a pseudo-steady state boundary can be produced by electrokinetic injection of the sample matrix directly from the sample well. This has been demonstrated with a single fluorescent neutral analyte, but the method should find widespread utility for stacking other neutral and charged species on the microchip format.

EXAMPLE NO. 2

Mode for Carrying Out the Experiment—Example No. 2

With regards to the material, Nanopure water (Barnstead/Thermolyne, Dubuque, Iowa) was used for all buffers. Sodium tetraborate, sodium hydroxide, punctilious ethanol and anhydrous methanol were obtained from Sigma Company (St. Louis, Mo.). Sodium dodecyl sulfate was obtained from Bio-Rad Laboratories (Hercules, Calif.). Corticosteroids were obtained from Steraloids, Inc. (Newport, R.I.).

With regards to the apparatus, all electrophoresis experiments were conducted with a Hewlett Packard HP 3D-CE instrument interfaced with a Hewlett Packard Kayak XA computer with HP 3D-CE ChemStation Rev. A.06.01[403] software for control of the instrument and data collection (Hewlett Packard, Waldbronn, Germany). Capillary temperature was maintained at 20° C. and detection was by UV absorption at 242 nm with a 20 nm bandwidth. The capillaries were 50 µm i.d. and 33 cm in length (24.5 cm to the detector), from Polymicro Technologies, Inc. (Phoenix, Ariz.). New capillaries were conditioned by flushing at ·1 bar with 1.0 M sodium hydroxide for sixty minutes, followed by water for 30 minutes. Capillaries were re-conditioned at the start of each day's experiments by flushing with 1.0 M sodium hydroxide and water for five minutes each.

With regards to the separation buffer and sample matrix parameters, the separation buffer vial volume was 700 µl. Separation buffers consisted of SDS and borate at concentrations as stated. Borate was prepared from sodium tetraborate, and concentrations are stated as borate (4 times the tetraborate concentration). The pH of separation buffers was ~9.0 except as stated. Anhydrous methanol was added to the separation buffer at stated percentages (v/v). Separation buffers were degassed by decompression in a syringe and passed through a 0.2 µm pore-diameter filter before use. The capillary was flushed with fresh separation buffer at ~1 bar for two minutes before each experiment. Separation polarity was normal (the anode was at the inlet). Separations occurred at 15 or 30 kV as stated. Separation buffer was in the inlet and outlet vials for all separations. EOF migration time was affirmed by the following two separate methods: distance the sample solvent moved through the capillary (24.5 cm to the detector, and 33 cm to the outlet) versus time of UV signal of the sample solvent at the detector, and the return to background current as the sample solvent exited the outlet[11], e.g., 105.6 seconds to the detector (24.5 cm), as determined by UV absorption, and 143.1 seconds as determined by the return to background current at the end of the capillary (33 cm). A two second pressure injection of separation buffer containing 10% organic (ethanol) was used to allow conductivity changes to be observed by the exit of the sample matrix solvent from the capillary under electrophoresis with the various separation buffers tested. The two methods corroborated EOF velocity with a precision between 99.8 and 98.7% for all buffers, with an average of 0.65% difference. Analyte migration time was adjusted for electrokinetic injection duration (e.g. a 20-second electrokinetic injection contributed to the movement of the sample solvent into the capillary by 20 s times the EOF velocity). Sample matrix vial volume was 150 to 700 µl. Sample matrixes were prepared with tetraborate, and concentrations were stated as borate. The pH of sample matrixes was ~9.0 to 9.2. Crystalline corticosteroids were dissolved in punctilious ethanol at 316 to 362 µg/ml in accordance with their molecular weight. Standards were stored at 4° C. when not in use. Aliquots were dried down to remove the organic solvent and dissolved in sample matrixes at stated concentrations. The electrokinetic injection polarity was normal (the anode was at the inlet). Injections were performed at 15 or 30 kV as stated. Injections were undertaken with the sample vial at the inlet, and the separation buffer vial used in the subsequent separation was at the outlet. Conductivity of solutions was determined with a Model 35 conductance meter (YSI Scientific, Yellow Springs, Ohio).

Results and Discussion—Example No. 2

Micelle concentration. Velocity of analytes can be decreased by increasing the concentration of the micelle in the separation buffer. On the other hand, it is desirable to use the lowest-possible micelle concentration to control excessive conductivity within the capillary, and subsequent deleterious joule heating. Hence, the effect of concentration of the micelle in the separation buffer, SDS, was examined. Separations of analytes with short pressure-injected sample plugs (ca. 1 to 2 mm) under non-stacking conditions (sample matrix 10% ethanol/water) with varied concentrations of SDS in the separation buffer were examined for minimum peak velocity in combination with minimum peak width. Borate was included at 20 mM in separation buffers to maintain pH ~9. The analytes exhibited decreasing velocity with increasing SDS concentration from 10 to 160 mM. Electropherograms from separations with a pressure-injected sample plug (20 seconds at 50 mbar, ~1.6 cm) were used to identify the individual analyte peaks with 40 mM SDS in the separation buffer (data not shown).

Figure 10:
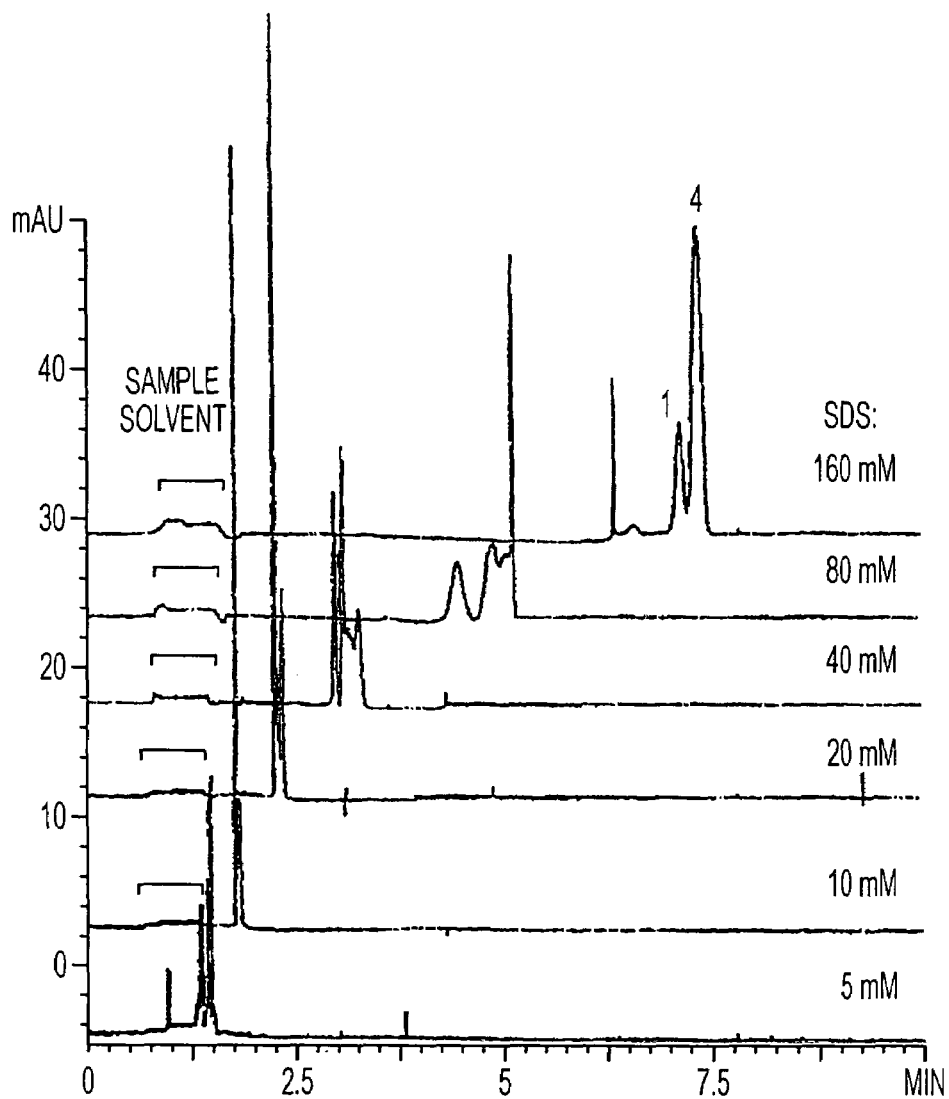
FIG. 10 is an electropherogram showing a graphical representation of absorbance (mAU) versus time to illustrate the effect of SDS concentration on analyte migration time. Separation buffer comprises: SDS at concentrations from 5 to 160 mM as shown in the figure, with 20 mM borate. The capillary is 50 μm by 33 cm. Borate sample matrix equivalent conductivity to each separation buffer. Injection for 40 seconds at 15 kV. The EOF velocity (for 5 to 160 mM SDS buffers) was as follows: 0.288, 0.285, 0.276, 0.265, 0.260, 0.260 cm/sec. The respective length of sample plug is 11.5 to 10.4 cm. Separation was at 15 kV and sample solvent zones are indicated in the figure. Migration time range for the slowest and fastest analytes are indicated by brackets below each electropherogram. Analyte concentrations were 1800 ppb, 1. Cortisol, and 4 Progesterone.

Electrokinetic injections at 15 kV for 40 seconds, (plug length ~10.5 to 11.5 cm), were also undertaken to predict the maximum injectable plug length for the analytes. As shown in FIG. 10, separation buffers contained 20 mM borate and SDS at 5, 10, 20, 40, 80, and 160 mM. Sample matrixes were adjusted with borate to maintain equivalent conductivity with the respective separation buffers. Selectivity was restricted by the use of SDS/borate separation buffers without further modification (e.g., cyclodextrins or other organic modifiers to improve peak resolution). This led to a poor resolution of the individual analytes. However, the range of the lowest- and highest-velocity analytes, cortisol, and progesterone, was taken by the appearance of the first and last peaks exhibiting UV absorption at the corticosteroid absorption maximum (242 nm) in each electropherogram as noted in FIG. 10.

An increase in SDS concentration in the separation buffer affected EOF velocity, which decreased from 0.288 cm/sec to 0.260 cm/sec for 5 mM SDS to 160 mM SDS separation buffers. With the 5 mM SDS buffer, analytes migrated with the sample solvent zone, consistent with the use of a sub-critical micelle concentration in the separation buffer. As can be seen in FIG. 10, analyte migration velocity decreases steadily with increasing SDS concentration. The EOF and peak velocities are shown in Table 7.

TABLE 7

Effect of SDS concentration on analyte migration time.

| SDS mM | $v_{EOF}$ (cm/sec) | $v_{cortisol}$ (cm/sec) | $v_{progesterone}$ (cm/sec) | $L_{max}$ (cm) (cortisol) | $L_{max}$ (cm) (progesterone) |
|---|---|---|---|---|---|
| 10 | 0.285 | 0.161 | 0.160 | 13.7 | 14.0 |
| 20 | 0.276 | 0.136 | 0.133 | 18.9 | 19.1 |
| 40 | 0.265 | 0.109 | 0.103 | 25.2 | 26.5 |
| 80 | 0.260 | 0.080 | 0.069 | 55.1 | 67.9 |
| 160 | 0.260 | 0.062 | 0.050 | 78.2 | 102.9 |

There is a logarithmic decrease in peak velocity with increasing SDS concentration. As can be seen from the data in Table 7, it is possible to make an 78.2 cm injection (3.2 effective capillary-lengths) with 160 mM SDS buffer. Further parameters of the separation buffer were investigated using the minimum SDS concentration (40 mM) required for an effective capillary-length (24.5 cm) injection.

Figure 11:
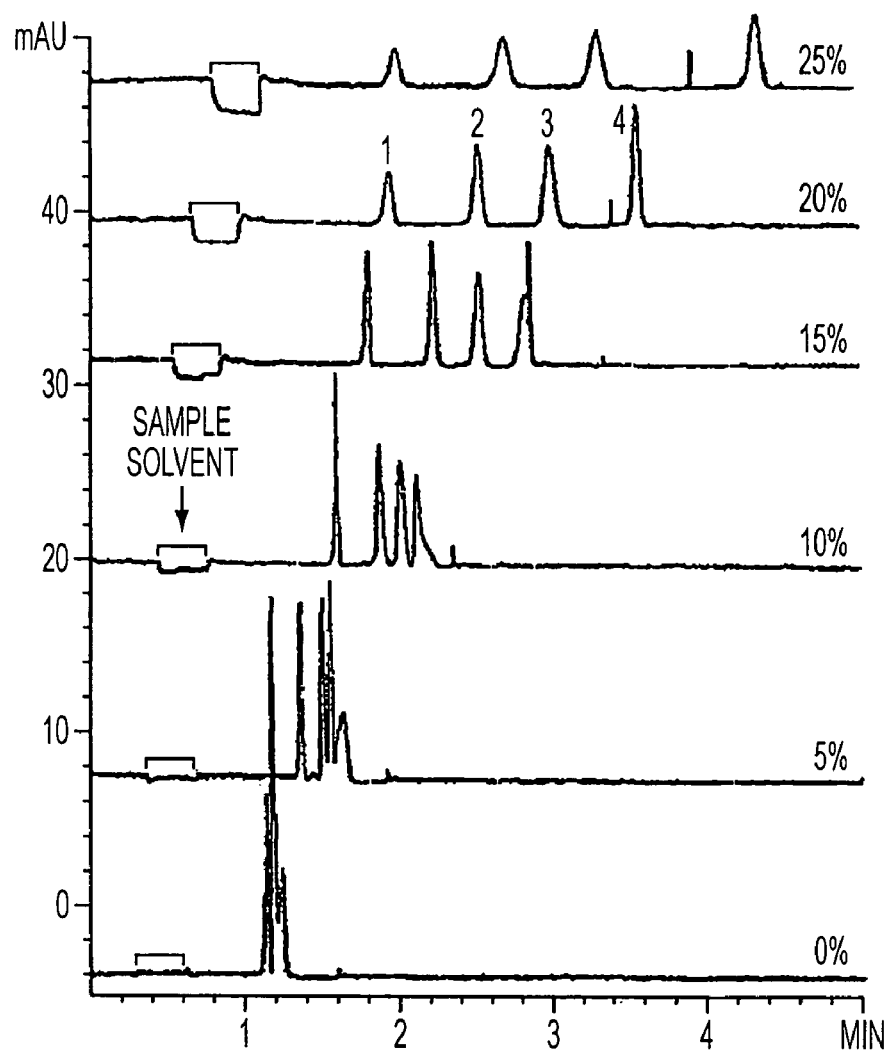
FIG. 11 is an electropherogram showing a graphical representation of absorbance (mAU) versus time for depicting the effect of methanol modification of the separation buffer. Separation buffers with 40 mM SDS and 20 mM borate, and augmented with 0, 5, 10, 15, 20, and 25% methanol as stated in the figure. Borate sample matrix was equivalent in conductivity to each separation buffer. Electrokinetic injection was at 30 kV for 20 seconds with separation at 30 kV. Analyte concentration was 1800 ppb. The peaks 1–4: cortisol, 11-deoxycortisol, 17α-hydroxyprogesterone, and progesterone. Sample solvent zone is indicated by brackets in the figure.

Effects of Methanol in the Separation Buffer. An organic modifier can increase the viscosity of the aqueous solvent, causing a decrease in the electroosmotic flow velocity. However, an increase in viscosity is not productive toward improving the efficiency of stacking efficiency because charged species in the separation buffer (i.e., the micelle) experience a decrease in mobility similar to that of the electroosmotic flow. It was considered whether the addition of an organic modifier might increase the affinity of the analytes for the micelle, thus allowing extended injection lengths. As shown in FIG. 11, methanol, a simple organic modifier, was included at 0, 5, 10, 15, 20, and 25% in a separation buffer containing 40 mM SDS and 20 mM borate. The addition of methanol caused a decrease in EOF velocity that was linear with methanol concentration at 0, 5, 10, 15, 20, and 25%, with $R^2=0.9973$. However, some analytes exhibited a decrease in velocity beyond that caused by the decrease in EOF. The ratio of the EOF to peak velocity of progesterone (the lowest-velocity analyte) ranged from 1.64 to 3.12 when the methanol concentration was varied from 0 to 25%. This indicated a 2.12-times effective capillary-length injection (52 cm) could be made per equation (10) if the separation buffer was augmented with 25% methanol. Unfortunately, the fastest migrating analyte, cortisol, was not affected by the addition of methanol, with the ratio of the EOF to peak velocity ratio remaining at 1.56 from 0 to 25% methanol. This indicated a maximum injection length of (1.56−1)*24.5 cm=13.8 cm could be made, regardless of methanol concentration in the separation buffer.

Effect of Borate Concentration in the Separation Buffer. Manipulations of EKC systems where hydrophobic interaction dictates analyte electrophoretic mobility, and hence analyte migration time, center on electrokinetic vector concentration and the addition of an organic modifier. While increasing SDS concentration in the separation buffer improved $L_{max}$ considerably, the effect on peak width of resolved analytes was not productive. The addition of methanol to the separation buffer allowed extended injection lengths for the more hydrophobic analytes, but did not affect mobility of the more-hydrophilic analytes. The effect of the concentration of the background electrolyte (borate, in this study) in conjunction with a fixed concentration of the micelle, SDS, in the separation buffer was examined. Separation buffers containing borate from 5 to 80 mM with 40 mM SDS were examined, with the borate concentration in respective sample matrixes adjusted to maintain equivalent conductivity with the separation buffer. There was a slight decrease in analyte velocity with increasing borate concentration from 5 to 80 mM (data not shown). The decrease in analyte velocity suggested the examination of higher-borate buffers. The effects of borate at concentrations of 80, 120, 160, 200, and 240 mM in the separation buffer with 40 mM SDS were examined, with sample matrix conductivity adjusted with borate to equivalent conductivity with the separation buffer.

Figure 12:
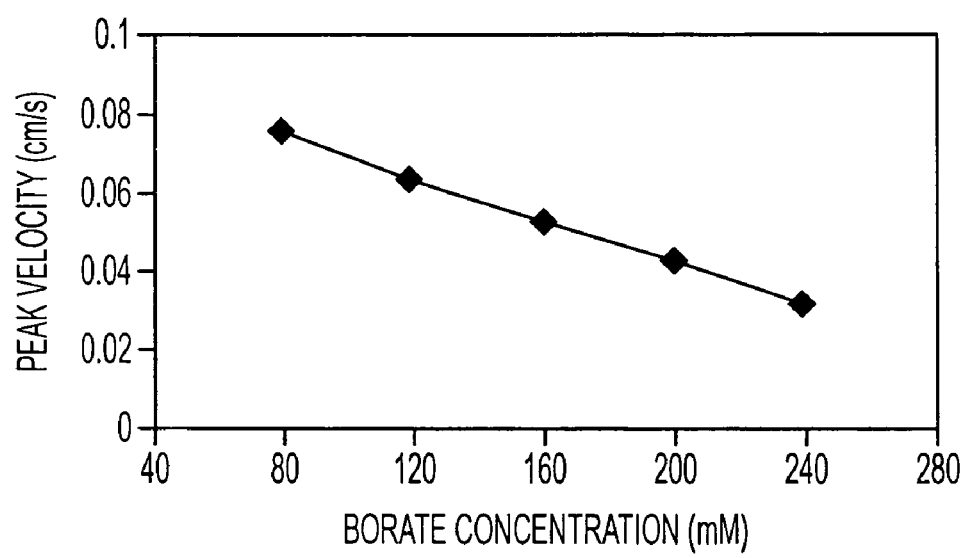
FIG. 12 is a graphical representation of peak velocity versus borate concentration for illustrating the effect of background electrolyte concentration on analyte velocity. The conditions further include 40 mM SDS separation buffer with borate at 80, 120, 160, 200 and 240 mM. Borate sample matrix had equivalent conductivity to each separation buffer. Progesterone at 270 ppb was used to calculate peak velocity (cm/sec) via the migration time. Electrokinetic injection for 20 minutes at 15 kV. Migration time was linear with borate concentration, $R^2$=0.9994.
Figure 13:
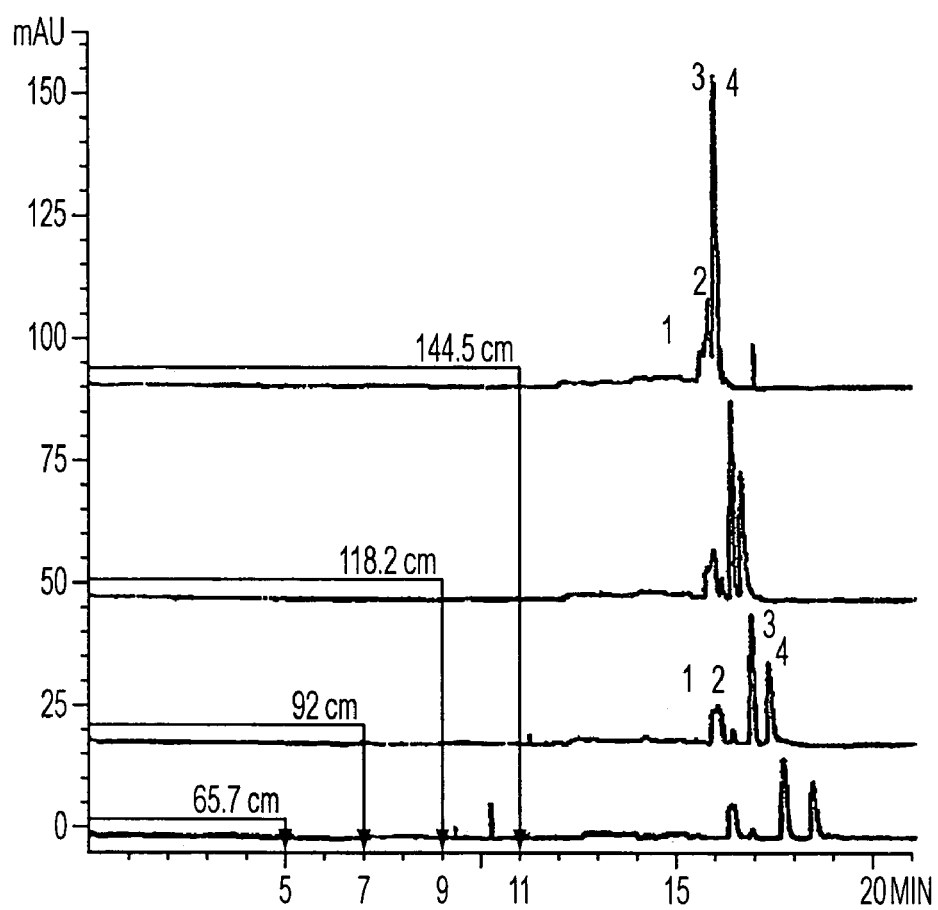
FIG. 13 is an electropherogram showing a graphical representation (absorbance (mAU) versus time) for illustrating electrokinetic injections with high-borate separation buffer. Separation buffer: 40 mM SDS in 240 mM borate at pH~9.2. Both injection and separation is at 15 kV. The injections were for 5, 7, 9, and 11 minutes, corresponding to injection plug lengths of 65.7 to 144.5 cm as indicated. Lines above each electropherogram correspond to the length of electrokinetic injection in minutes. The length in cm for each injection is listed above each bracket. The arrow extending downward from the right-side of each line points to the time the inlet vial was switched from the sample matrix to separation buffer. The sample matrix consists of 270 mM borate with analytes at ~270 ppb. Further included are peaks 1–4: cortisol, 11-deoxycortisol, 17α-hydroxyprogesterone, and progesterone. The EOF velocity is established at 0.219 cm/sec as per the text.

There was an effect of borate concentration on the EOF velocity, which decreased from 0.245 cm/sec with the 80 mM borate separation buffer, to 0.219 cm/sec with the 240 mM borate separation buffer. The velocity of the analytes, however, was decreased by higher concentrations of borate in the separation buffer beyond the effect of the high-borate in decreasing EOF velocity. As can be seen in FIG. 12, the velocity of progesterone exhibits a decrease in velocity that is linear with increasing borate concentration. In addition, the faster-migrating analytes exhibit significantly decreased velocity. With the 240 mM borate separation buffer, the decreased analyte velocities in conjunction with minimal reduction of EOF velocity allowed for multiple capillary-length injections prior to separation of the analytes. Continuous conductivity sample matrixes (~270 mM borate) containing analytes at 270 ppb were injected into a separation buffer containing 40 mM SDS and 240 mM borate. Injections from 65.7 to 197 cm were investigated. These represent injections ~2 to 6-times the volume of the capillary. FIG. 13 shows the effect of increased injection length on analyte peak height and resolution for injected plugs of 65.7 to 144.5 cm. Electropherograms include the sample injection (i.e., the UV absorption was recorded from the initiation of sample matrix injection at t=0). Injection duration is indicated by the length of the line above each electropherogram, with an arrow pointing down to the time axis to indicate the end of each electrokinetic injection. At this point, the inlet was switched from the sample matrix to the separation buffer and separation commenced. Injection plug lengths as determined by an EOF injection velocity of neutral analytes at 0.219 cm/sec are indicated above each electropherogram. Peak height of analytes 3 and 4 increases with increasing injection length. For the 144.5 cm injection, 17α-hydroxyprogesterone and progesterone (peaks 3,4) at 270 ppb are separated, with signal to noise of ~300:1. Calculated peak width at half height indicates a concentration factor of ~1500 (144.5 cm reduced to 0.098 cm).

Under continuous conductivity conditions the minimum analyte velocity is simply the sum of the electroosmotic flow electrophoretic mobility plus the electrophoretic mobility of the electrokinetic vector (SDS), times the applied electric field. The relationship between the velocity of the electrokinetic vector and the distance into the capillary at which the electrokinetic vector at the boundary with the sample matrix co-ion (borate) exists after completely transiting the sample solvent plug is given by:

$$L_{trans} = t_{trans} * [(\mu_{EOF} + \mu_{ekv}) * E] \tag{13}$$

where $L_{trans}$ is the distance into the capillary the sample matrix co-ion/SDS boundary has moved at the conclusion of stacking, $t_{trans}$ is the amount of time it takes for the SDS to transit the sample plug (dependent on the sample plug length), $\mu_{EOF}$ and $\mu_{ekv}$ are the intrinsic mobilities of the EOF and the micelle, and E is the applied field. The $t_{trans}$ can be determined with the length of the sample plug injected, $L_{plug}$:

$$(t_{trans} = L_{plug} / \mu_{ekv} * E) \tag{14}$$

As analytes must partition out of the micelle to allow separation, the effective mobility of uncharged analytes are less than that of the electrokinetic vector. It is possible to adapt equation (2) to determine analyte/micelle complex velocities:

$$L_{trans} = t_{trans} * v_{a/ekv} \tag{15}$$

where $v_{a/ekv}$ is the velocity of the analyte/electrokinetic vector complex. The velocity of the analyte/electrokinetic vector complex, $v_{a/ekv}$, can be determined by observing the time of appearance of the analyte peak at the detector under continuous electrokinetic injection from the sample matrix vial through the detector.

It is likewise possible to adapt equation (14) to:

$$(t_{trans} = L_{plug} / v_{a/ekv}) \tag{16}$$

where $L_{plug}$ is determined by the velocity of the EOF multiplied by the duration of the injection in seconds.

Experimental Corroboration of Equation (10). Equation (10) was used to predict the maximum plug length injection with the 40 mM SDS/240 mM borate separation buffer:

$$[(v_{EOF}, 0.219 \text{ cm/sec}/v_{a/ekv}, 0.0261 \text{ cm/sec})-1]*24.5 \text{ cm (length to detector)}=180 \text{ cm } (L_{max}) \quad (17)$$

Figure 14:
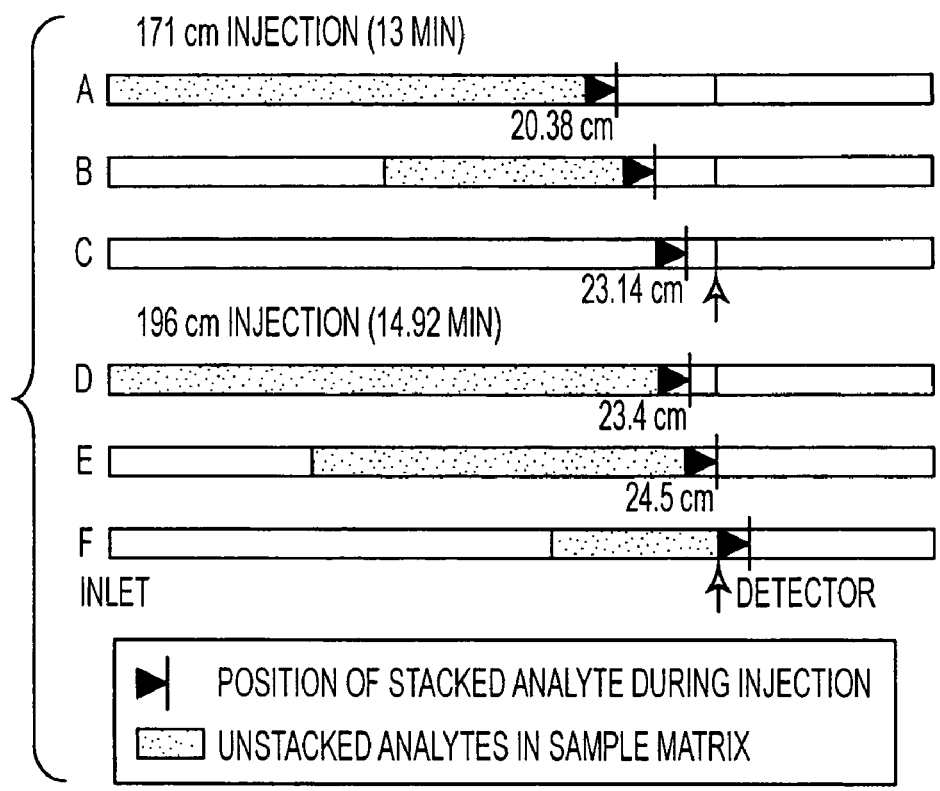
FIGS. 14A–14F are schematic depictions of the position of stacked analyte/micelle peak during extended injections. A 33 cm capillary with a 24.5 cm effective length is depicted. The detector position is indicated by vertical arrows.
Figure 15:
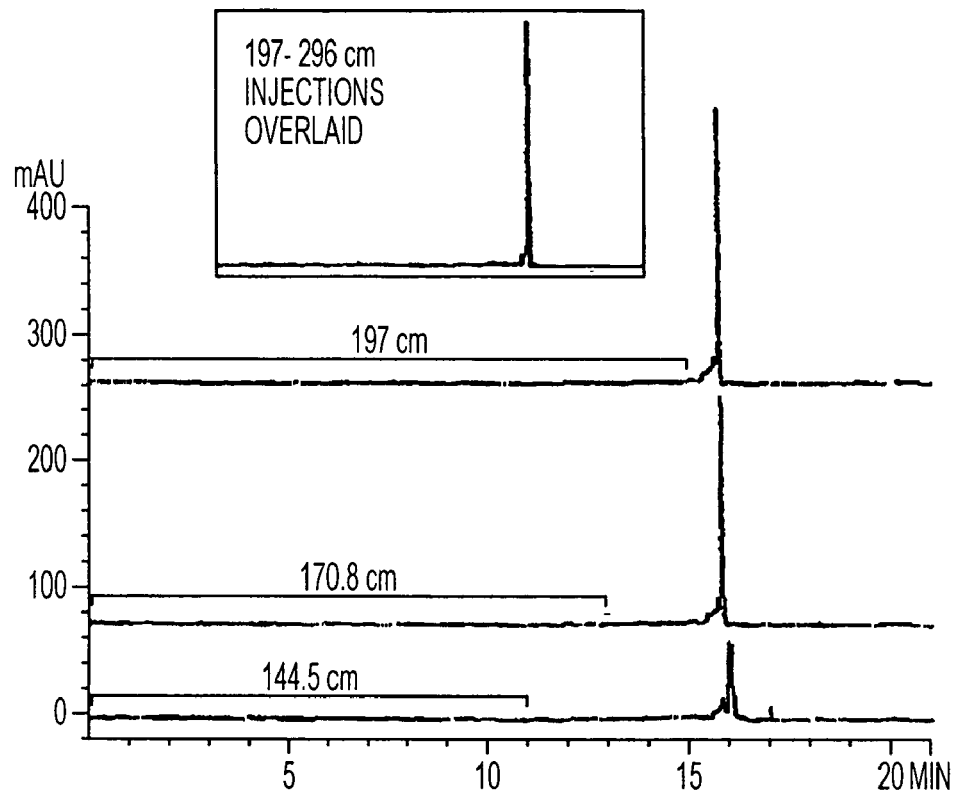
FIG. 15 is an electropherogram of absorbance (mAU) versus time for demonstrating the empirical corroboration of maximum injection length. The 144.5 cm injection does not exceed the length required for the injection-side of the sample plug to transit the analyte/micelle peak before it reaches the detector, and there is adequate distance remaining within the capillary to allow separation of the analytes following the sample injection. The 171 cm injection exhibits a slightly lower peak height than the 197 cm injection, as explained in the text. Injections beyond 180 cm are predicted to be identical. The Inset depicts injections of 196, 223, 250, and 276 cm, overlaid.

With the 240 mM borate separation buffer, the migration time for the progesterone peak averaged 15.62 minutes for injections ranging from 15 to 21 minutes (197 to 276 cm injected plug length). This gave a velocity of 0.0261 cm/sec for the progesterone/SDS complex. The ratio of $v_{a/ekv}$ to $v_{EOF}$ times the length of the capillary to the detector (24.5 cm) gives the distance the stacked progesterone/SDS peak moves into the capillary for each effective capillary-length injection. The distance in this case is 2.93 cm. Referring to FIG. 14, the transition of the analyte/electrokinetic vector complex into the capillary with different length injections is depicted according to horizontal bars A, B, and C. It is possible to inject by EOF until an analyte/electrokinetic vector complex is still far enough from the detector window that the injection-side of the sample plug can transit the stacked analyte/micelle complex before the complex reaches the detector. For an injection of 171 cm (13 minutes, horizontal bars A, B, and C), the analyte/micelle complexes are just 4.1 cm away from the window at the conclusion of injection and commencement of separation (by switching the inlet vial from the sample matrix to separation buffer). An additional 9.8 cm of sample matrix can be stacked before the analyte/electrokinetic vector complexes reach the 2.93 cm mark for the 171 cm injection. Still referring to FIG. 14, as shown with horizontal bars D, E, and F, injections greater than 180 cm (13.7 minutes) do not allow the entire sample matrix solvent to pass through the stacking analyte/micelle complexes before the complexes reach the detector. Injections that continue long enough to move the analyte/micelle complexes closer than 2.93 cm to the detector will therefore appear identical to each other. As can be seen in FIG. 15, while the 171 cm injection is similar to the 197 cm injection, the peak height is less, reflecting the 9.8 cm effective shorter sample plug for the 171 cm injection. The progesterone/ micelle complex migration times for injections from 15 to 21 minutes (197 to 276 cm) are nearly identical, with a coefficient of variation of only 0.26%. Peak height of progesterone for these injections, with an average height of 198.8 mAU, had a coefficient of variation of 5.75%. Actual sample matrix volume for a 180 cm injection is ~3.5 µl.

Mechanism of Analyte/Micelle Complex Velocity Reduction by Borate. The analytes used in this study exhibit negligible affinity for the borate ion, yet enhancing analyte interaction with the micellar phase (increased k-value) would cause a decrease in velocity. Increased hydrophobic interaction with the micelle may result from an increase in surface tension of the solvent by the presence of high salt concentrations. It would also be possible to decrease the velocity of analyte/electrokinetic vector complexes by increasing the mobility of the electrokinetic vector. In either case, the ratio of electroosmotic flow to analyte/electrokinetic vector velocity would be increased. However, high borate concentrations could also have an effect on decreasing the electroosmotic flow rate.

Therefore, the effect of high borate on both the electroosmotic flow and analyte/electrokinetic vector complex mobility was examined. It is possible to examine these parameters by converting equation (10) from velocities to electrophoretic mobilities:

$$L_{max}=([\mu_{EOF}/(\mu_{EOF}+\mu_{a/ekv})]-1)*L_{det} \quad (18)$$

where $\mu_{EOF}$ is the electrophoretic mobility of electroosmotic flow, and $\mu_{a/ekv}$ is the apparent electrophoretic mobility of the analyte/electrokinetic vector complex. The $\mu_{EOF}$ was determined by dividing the velocity of the sample solvent by the applied electric field. The $\mu_{a/ekv}$ was determined with continuous sample matrix injections into separation buffer until the analyte/electrokinetic vector complex appeared at the detector window. The distance the analyte/electrokinetic vector complex traveled "upstream" of electroosmotic flow to the detector window was calculated by multiplying the electroosmotic flow velocity by the time (in seconds) required for the complex to reach the detector window. One was subtracted from this ratio to correct for the translation of the analyte/electrokinetic vector from the capillary inlet to the detector window. This sum was multiplied by the capillary length to the detector to give the maximum injection length. The µ is expressed in cm²/V*sec.

An example of how this data was used is included. Equation (18) is simply a transformation of equation (10), utilizing the same data to determine results. For the separation buffer with 240 mM borate and 40 mM SDS, the mobility of EOF ($\mu_{EOF}$) was first determined by dividing the velocity of the sample solvent by the electric field:

$$\mu_{EOF}=(0.219 \text{ cm/sec})*(33.0 \text{ cm}/15000 \text{ } V)=4.82\times10^{-4} \text{ cm}^2/V*\text{sec} \quad (19)$$

For determining the $\mu_{a/ekv}$, it is necessary to determine the distance the progesterone/micelle complex traveled from the injection point (capillary inlet) to the detection window. This distance is the same as the maximum injectable plug length, 180 cm. In this case, the negatively-charged progesterone/ micelle complex was moving against electroosmotic flow for 15.62 minutes (937 sec), during which time 180 cm of sample solvent was traversed. The electrophoretic mobility of the analyte/micelle complex can now be determined by:

$$\mu_{a/ekv}=(-180 \text{ cm}/937 \text{ sec})*(33.0 \text{ cm}/15000 \text{ } V)=-4.23\times10^{-4} \text{ cm}^2/V*\text{sec} \quad (20)$$

With a buffer consisting of 40 mM SDS buffer and 80 mM borate, $\mu_{EOF}$ was $5.21\times10^{-4}$ cm²/V*sec, and $\mu_{a/ekv}$ was $-3.66*10^{-4}$ cm²/V*sec. Maximum injectable plug length with this separation buffer (57.5 cm) is reduced ~3-fold compared to the 40 mM SDS/240 mM borate buffer due to the 15.5% decrease in $\mu_{a/ekv}$ versus the 8% increase in $\mu_{EOF}$. There is an exponential increase in maximum injectable plug length as the ratio of $\mu_{EOF}$ to ($\mu_{EOF}+\mu_{a/ekv}$) increases. Predictions from the data in FIG. 13 and equation (18) indicate that maximum injection plug lengths can approach five meters in a capillary with an effective length of 24.5 cm using a separation buffer containing 40 mM SDS and 300 mM borate. As the quantity $\mu_{EOF}+\mu_{a/ekv}$ nears zero, stacking is infinite, and separation is impossible. If the quantity is negative, stacking analytes will move out of the injection end of the capillary.

EXAMPLE NO. 2

Conclusions

Extreme attenuation of analyte zones is obtained by extended electrokinetic stacking injection in EKC. Separation buffer parameters were investigated to allow extended injection plug lengths with continuous conductivity sample matrixes. As analytes are injected by electroosmotic flow into the separation buffer, each analyte exhibits a decrease in velocity due to the interaction with the micelles in the separation buffer. To determine maximum-length injections, the velocity of each analyte/electrokinetic vector complex must be considered. Equations have been introduced to determine the maximum injection length per individual analyte/micelle complexes.

A simple relationship exists between the velocity of the electrokinetic injection vector and the resultant velocity of analytes that encounter an electrokinetic vector that imparts a mobility that is opposite that of the injection vector. This relationship determines the maximum injectable plug length. It can be expressed in terms of velocity (equation 10), or in terms of electrophoretic mobility (equation 18). In general terms for electrophoresis:

$$L_{max} = (\mu_{inj}/\mu_{orth} - 1) * L_{det} \qquad (21)$$

where $L_{max}$ is the injection length at which the injector-end of the sample plug arrives at the detector simultaneous to the conclusion of stacking, $\mu_{inj}$ is the electrophoretic mobility of the analyte during the injection process, and $\mu_{orth}$ is the electrophoretic mobility of the analyte in the stacking process as it encounters a counter-mobility vector. This type of system is referred to as an orthogonal analyte stacking/injection system (OAS/IS). For electrokinetic chromatography in capillary electrophoresis, total sample solvent injections in the microliter range can now be made. Stacking of analyte zones from 144.5 cm to less than a millimeter in width has been demonstrated with an effective capillary length of only 24.5 cm. Maximum injection of ~7 effective capillary-lengths has been demonstrated. The implications for further miniaturization of electrophoretic processes on the microchip format are promising.

One skilled in the art would appreciated that the various materials and systems discussed herein are intended to exemplary and should not be limited thereto.

One skilled in the art would appreciate that the present invention discussed herein, including the various embodiments and examples, may be applied in certain aspects to gel electrophoresis and capillary electrochromatography methods and systems.

An advantage of the present invention electrokinetic injection method is that it is faster than previous injection methods by approximately an order of magnitude.

Another advantage of the present invention method is that it allows the loading of multiple-capillary volumes of sample for the first time.

Moreover, another advantage of the present invention method is that it provides a higher resolution for injection of large sample plugs in capillary electrophoresis, providing a faster and higher sensitivity injection mode in capillary electrokinetic chromatography.

Previously, long sample plugs could be injected into a capillary by pressure, with post-injection stacking of analytes occurring due to electrophoretic phenomena. However, the present invention provides that stacking can be initiated with injection, rather than post-injection. The present invention further provides that electrokinetic injection of neutral analytes with concomitant stacking of neutral analytes can be initiated at the commencement of injection.

Further still, the present invention method provides an electrokinetic injection of neutral analytes by electroosmotic flow in the presence of an orthogonal stacking system, e.g., an anionic electrokinetic vector in the separation buffer, constitutes an orthogonal analyte stacking/injection system (OAS/IS). The primary conditions are simply that the electrokinetic vector in the separation buffer has an opposing mobility to the analyte injection force, and that a suitable stacking boundary is formed between the injected sample and the electrokinetic vector in the separation buffer. As discussed herein, an extensive list of conditions for OAS/IS is provided (e.g., Tables 1–6). With properly instituted OAS/IS conditions, it is actually possible to inject sample plugs that are longer than the entire capillary.

Finally, the present invention provides a method of stacking injections for neutral analytes on the microchip format, with all the advantages of the OAS/IS described for the capillary format translatable to the microchip format without modification, including cationic and anionic analytes, as described in Tables 1 through 3.

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced herein.

We claim:

1. A method of stacking analytes in electrophoresis, comprising:
    filling a conduit with a separation buffer, said buffer comprising buffer components;
    orienting a first end of said conduit in operative relation with said separation buffer;
    orienting a second end of said conduit in operative relation with an analyte sample;
    applying an electric field across said separation buffer and said analyte sample, wherein:
        portions of said analytes sample injected into said second end of said conduit, whereby the velocity of said injected analytes sample defines an injection vector, and
        said buffer components have a net movement opposite that of the injection vector, whereby analytes being injected encounter said buffer component and experience a decrease in velocity, said decrease in velocity constitutes a vector known as a stacking vector; and
    adjusting the mobility of either said injection vector or said stacking vector to allow maximum length of said analytes being injected.

2. The method of claim 1, further comprising means for radiating said analytes within said conduit.

3. The method of claim 2, further comprising means for detecting said radiation of said analytes.

4. The method of claim 3, further comprising means for storing data detected by said detecting means.

5. The method of claim 1, wherein said electric field is in a range between about −5000 V/cm to about 5,000 V/cm.

6. The method of claim 1, wherein said buffering components comprise sodium borate, sodium phosphate, and/or Tris/TRIZMA or combination thereof.

7. The method of claim 1, wherein said injection vector comprises sodium dodecyl sulfate, sodium cholate, borate, and/or tetraborate, or combination thereof.

8. The method of claim 1, wherein said analyte sample an is anionic, neutral, zwitterionic or cationic.

9. The method of claim 1, wherein said injection vector is cationic, anionic, neutral, or zwitterionic.

10. The method of claim 1, wherein said analyte sample is prepared with said buffer components, said buffer components are buffering agents or salts to maintain conductivity equal to or higher than said buffer.

11. The method of claim 10, wherein said analyte sample further comprises a biological or an additional sample with a native salt concentration.

12. The method of claim 11, wherein said analytes comprise a costicosteroid.

13. The method of claim 12, wherein said costicosteroid comprises progesterone, 17-α-hydroxyprogesterone, 11-deoxycortisol, or cortisol or any combination thereof.

14. The method of claim 10, wherein the analyte sample further comprises a buffering agent and higher mobility co-ion.

15. The method of claim 14, wherein said higher mobility co-ion comprises at least one of phosphate, sulphate, cyclodextrins, fluoride, chloride, bromide, or iodide, or any combination thereof.

16. The method of claim 1, wherein said injection of said analyte sample injects by electroosmotic flow.

17. The method of claim 16, wherein said injection occurs under said electric field with normal polarity, whereby under normal polarity a cathode being in contact with said first end and an anode being in contact with said second end.

18. The method of claim 16, wherein said injection occurs under said electric field with reverse polarity, whereby under reverse polarity an anode being in contact with said first end and a cathode being in contact with said second end.

19. The method of claim 16, wherein said analyte sample is anionic, neutral, zwitterionic or cationic.

20. The method of claim 16, wherein said injection vector is cationic, anionic, neutral, or zwitterionic.

21. The method of claim 1, wherein said injection of said analyte sample injects by electroosmotic flow and pressure.

22. The method of claim 21, wherein said pressure is in a range between about 0 to about 1000 mbar above atmospheric pressure.

23. The method of claim 21, wherein said injection occurs under said electric field with positive pressure and normal polarity, whereby under normal polarity a cathode being in contact with said first end and an anode being in contact with said second end, and whereby under positive pressure said pressure being applied with said second end.

24. The method of claim 21, wherein said injection occurs under said electric field with negative pressure and normal polarity, whereby under normal polarity a cathode being in contact with said first end and an anode being in contact with said second end, and whereby under negative pressure said pressure being applied with said first end.

25. The method of claim 21, wherein said injection occurs under said electric field with positive pressure and reverse polarity, whereby under reverse polarity an anode being in contact with said first end and a cathode being in contact with said second end, and whereby under positive pressure said pressure being applied with said second end.

26. The method of claim 21, wherein said injection occurs under said electric field with negative pressure and reverse polarity, whereby under reverse polarity an anode being in contact with said first end and a cathode being in contact with said second end, and whereby under negative pressure said pressure being applied with said first end.

27. The method of claim 21, wherein said analyte sample is anionic, neutral, zwitterionic or cationic.

28. The method of claim 21, wherein said injection vector is cationic, anionic, neutral, or zwitterionic.

29. The method of claim 21, wherein said pressure is in a range between about 1 to about 500 mbar above atmospheric pressure.

30. The method of claim 1, wherein said injection of said analyte sample injects in the absence of electroosmotic flow and pressure or reduced electroosmotic flow and pressure.

31. The method of claim 30, wherein said pressure is in a range between about 0 to about 1000 mbar above atmospheric pressure.

32. The method of claim 30, wherein said injection occurs under said electric field with positive pressure and normal polarity, whereby under normal polarity a cathode being in contact with said first end and an anode being in contact with said second end, and whereby under positive pressure said pressure being applied with said second end.

33. The method of claim 30, wherein said injection occurs under said electric field with negative pressure and normal polarity, whereby under normal polarity a cathode being in contact with said first end and an anode being in contact with said second end, and whereby under negative pressure said pressure being applied with said first end.

34. The method of claim 30, wherein said injection occurs under said electric field with positive pressure and reverse polarity, whereby under reverse polarity an anode being in contact with said first end and a cathode being in contact with said second end, and whereby under positive pressure said pressure being applied with said second end.

35. The method of claim 30, wherein said injection occurs under said electric field with negative pressure and reverse polarity, whereby under reverse polarity an anode being in contact with said first end and a cathode being in contact with said second end, and whereby under negative pressure said pressure being applied with said first end.

36. The method of claim 30, wherein said analyte sample is anionic, neutral, zwitterionic or cationic.

37. The method of claim 30, wherein said injection vector is cationic, anionic, neutral, or zwitterionic.

38. The method of any of claims 16, 21, or 30, further comprising modification of electroosmotic flow by pressure.

39. The method of any of claims 16, 21, or 30, further comprising modification of electroosmotic flow by chemically or covalently dynamically coating of said conduit.

40. The method of claim 30, wherein said pressure is in a range between about 1 to about 500 mbar above atmospheric pressure.

41. The method of claim 1, further comprising modification of said injection vector by modification of said analyte sample by inclusion of a background electrolyte or a high-mobility co-ion.

42. The method of claim 1, further comprising modification of said injection vector by modification of said buffer by addition of an organic modifier or increase in background electrolyte.

43. The method of claim 1, wherein said injection vector includes a neutral species affecting said electrophoretic mobility of a charged species.

44. The method of claim 1, wherein said electric field is in a range between about 10 V/cm to about 1000 V/cm.

45. An apparatus for stacking analytes in electrophoresis, comprising:
means for filling a conduit with a separation buffer, said buffer comprising buffer components;
means for orienting a first end of said conduit in operative relation with said separation buffer;
means for orienting a second end of said conduit in operative relation with an analyte sample;
means for applying an electric field across said separation buffer and said analyte sample, wherein:

portions of said analytes samples inject into said second end of said conduit, whereby the velocity of said analytes defines an injection vector, and said buffer components have a net movement opposite that of the injection vector, whereby analytes being injected encounter said buffer component and experience a decrease in velocity, said decrease in velocity constitutes a vector known as a stacking vector; and means for adjusting the mobility of either said injection vector or said stacking vector to allow maximum length of said analytes being injected.

46. The apparatus of claim 45, further comprising means for radiating said analytes in said conduit.

47. The apparatus of claim 46, further comprising means for detecting said radiated analyte.

48. The apparatus of claim 47, further comprising means for storing data generated by said detecting means.

49. An apparatus for stacking analytes in electrophoresis, comprising:
a microfluidic device having at least a sample channel and a separation channel disposed therein, said sample and separation channels intersecting one another to form an intersection;
each of said sample and separation channels having an entrance and exit end;
said sample channel entrance end having a sample reservoir comprising sample in communication thereof;
said sample channel exit end having a waste reservoir comprising buffer in communication thereof;
said separation channel entrance end having a inlet reservoir comprising buffer in communication thereof; and
said separation channel exit end having an outlet reservoir comprising buffer in communication thereof;
electrode means for generating a voltage potential, between said sample reservoir and said outlet reservoir, and between said inlet reservoir and said outlet reservoir wherein:
portions of said analytes sample inject into said entrance end of said sample channel, whereby the velocity of said sample defines an injection vector, and
said buffer has a net movement opposite that of the injection vector, whereby sample injected encounter said buffer and experience a decrease in velocity, said decrease in velocity constitutes a vector known as a stacking vector; and
means for adjusting the mobility of either said injection vector or said stacking vector to allow maximum length of said analytes being injected.

50. The method of claim 49, further comprising means for radiating said sample in said separation channel.

51. The apparatus of either claim 49, further comprising a means for detecting said sample in said sample channel.

52. The apparatus of either claim 51, further comprising means for storing data generated by said detecting means.

53. A method of stacking analytes in electrophoresis, comprising:
filling a microfluidic device, having at least a sample channel and a separation channel disposed therein, said sample and separation channels intersecting one another to form an intersection with a separation buffer;
each of said sample and separation channels having an entrance and exit end,
said sample channel entrance end having a sample reservoir comprising sample in communication thereof;

said sample channel exit end having a waste reservoir comprising buffer in communication thereof;
said separation channel entrance end having a inlet reservoir comprising buffer in communication thereof; and
said separation channel exit end having an outlet reservoir comprising buffer in communication thereof;
means for applying an electric field across said sample reservoir and said outlet reservoir, and between said inlet reservoir and said outlet reservoir;
generating a first voltage potential between said sample reservoir and said outlet reservoir, wherein:
portions of said analytes sample inject into said entrance end of said sample channel, whereby the velocity of said sample defines an injection vector, and
said buffer has a net movement opposite that of the injection vector, whereby sample injected encounter said buffer and experience a decrease in velocity, said decrease in velocity constitutes a vector known as a stacking vector; and
generating a second voltage potential between said inlet reservoir and said outlet reservoir, wherein:
portions of said sample in said sample channel, flow through said intersection into said separation channel toward said exit end of said separation channel; and
adjusting the mobility of either said injection vector or said stacking vector to allow maximum length of said analytes being injected.

54. The method of claim 53, further comprising means for radiating said sample in said separation channel.

55. The method of claim 54, further comprising means for detecting said radiated sample.

56. The method of claim 55, further comprising means for storing data generated by said detecting means.

57. The method of claim 53, wherein said electric field is in a range between about −5,000 V to about 5,000 V.

58. The method of claim 53, wherein buffer component comprises sodium borate, sodium phosphate, and/or Tris/TRIZMA or combination thereof.

59. The method of claim 53, wherein said injection vector comprises sodium dodecyl sulfate, sodium cholate, borate; and/or tetraborate, or combination thereof.

60. The method of claim 53, wherein said analytes are anionic, neutral, zwitterionic or cationic.

61. The method of claim 53, wherein said injection vector is cationic, anionic, neutral, or zwitterionic.

62. The method of claim 53, wherein said analytes are prepared with said buffering agent or salt to maintain conductivity equal to or higher than said buffer.

63. The method of claim 62, wherein said analytes further comprises biological or additional samples with a native salt concentration.

64. The method of claim 63, wherein said analytes comprises a costicosteroid.

65. The method of claim 64, wherein said costicosteroid comprises at least one of progesterone, 17-α-hydroxyprogesterone, 11-deoxycortisol, or cortisol or any combination thereof.

66. The method of claim 62, wherein said analytes further comprises a buffering agent and higher mobility co-ion.

67. The method of claim 66, wherein said higher mobility co-ion comprises at least one of phosphate, sulfate, cyclodextrins, fluoride, chloride, bromide, or iodide or any combination thereof.

68. The method of claim 53, wherein said injection of said analytes inject by electroosmotic flow.

69. The method of claim 68, wherein said injection occurs under an electric field, whereby said cathode being in contact with said sample reservoir and said anode being in contact with said outlet reservoir.

70. The method of claim 68, wherein separation occurs under said electric field, whereby an anode being in contact with said inlet reservoir and a cathode being in contact with said outlet reservoir.

71. The method of claim 68, wherein said analytes are anionic, neutral, zwitterionic or cationic.

72. The method of claim 68, wherein said injection vector is cationic, anionic, neutral, or zwitterionic.

73. The method of claim 53, wherein said injection of said analytes injects by electroosmotic flow and pressure.

74. The method of claim 73, wherein said pressure is in a range between about 0 to about 1000 mbar above atmospheric pressure.

75. The method of claim 73, wherein said injection occurs under an electric field with positive pressure, whereby a cathode being in contact with said sample reservoir and an anode being in contact with said outlet reservoir, and whereby under positive pressure said pressure being applied with said sample reservoir.

76. The method of claim 73, wherein said injection occurs under an electric field with negative pressure, whereby a cathode being in contact with said sample reservoir and an anode being in contact with said outlet reservoir, and whereby under negative pressure.

77. The method of claim 73, wherein said analytes are anionic, neutral, zwitterionic or cationic.

78. The method of claim 73, wherein said injection vector is cationic, anionic, neutral, or zwitterionic.

79. The method of claim 73, wherein said pressure is in a range between about 1 to about 500 mbar above atmospheric pressure.

80. The method of claim 53, wherein said injection of said analytes injects in the absence of or reduced electroosmotic flow and pressure.

81. The method of claim 80, wherein said pressure is in a range between about 0 to about 1000 mbar above atmospheric pressure.

82. The method of claim 80, wherein said injection occurs under an electric field with positive pressure, whereby under a cathode being in contact with said sample reservoir and an anode being in contact with said outlet reservoir, and whereby under positive pressure said pressure being applied with said sample reservoir.

83. The method of claim 80, wherein said injection occurs under an electric field with negative pressure, whereby a cathode being in contact with said sample reservoir and an anode being in contact with said outlet reservoir; and whereby under negative pressure.

84. The method of claim 80, wherein said analytes are anionic, neutral, zwitterionic or cationic.

85. The method of claim 80, wherein said injection vector is cationic, anionic, neutral, or zwitterionic.

86. The method of any of claims 68, 73, or 80, further comprising controlling electroosmotic flow by coating said sample channel or using a restriction in said sample channel.

87. The method of claim 53, wherein an electric field is in a range between about 10 V/cm to about 1,000 V/cm.

88. The method of claim 80, wherein said pressure is in a range between about 1 to about 500 mbar above atmospheric pressure.

89. The method of claim 53, further comprising modification of said injection vector by modification of said analyte sample by inclusion of a background electrolyte or a high-mobility co-ion.

90. The method of claim 53, further comprising modification of said injection vector by modification of said buffer by addition of an organic modifier or increase in background electrolyte.

91. The method of claim 53, wherein said injection vector includes a neutral species affecting said electrophoretic mobility of a charged species.

* * * * *